US009259459B2

(12) United States Patent
Keler et al.

(10) Patent No.: US 9,259,459 B2
(45) Date of Patent: Feb. 16, 2016

(54) ANTIBODY VACCINE CONJUGATES AND USES THEREFOR

(75) Inventors: Tibor Keler, Ottsville, PA (US); Michael Endres, Riegelsville, PA (US); Lizhen He, Allentown, PA (US); Venky Ramakrishna, Riegelsville, PA (US)

(73) Assignee: Celldex Therapeutics Inc., Needham, MA (US)

( * ) Notice: Subject to any disclaimer, the term of this patent is extended or adjusted under 35 U.S.C. 154(b) by 1222 days.

(21) Appl. No.: 10/903,191

(22) Filed: Jul. 30, 2004
(Under 37 CFR 1.47)

(65) Prior Publication Data

US 2005/0180983 A1    Aug. 18, 2005

Related U.S. Application Data

(63) Continuation-in-part of application No. 10/769,144, filed on Jan. 30, 2004.

(60) Provisional application No. 60/443,979, filed on Jan. 31, 2003.

(51) Int. Cl.
| | | |
|---|---|---|
| C07K 14/52 | (2006.01) | |
| A61K 39/00 | (2006.01) | |
| C07K 14/59 | (2006.01) | |
| C07K 16/28 | (2006.01) | |

(52) U.S. Cl.
CPC .......... *A61K 39/0006* (2013.01); *A61K 39/0011* (2013.01); *C07K 14/59* (2013.01); *C07K 16/28* (2013.01); *C07K 16/2851* (2013.01); *A61K 2039/5154* (2013.01); *A61K 2039/6056* (2013.01); *C07K 2317/622* (2013.01); *C07K 2317/73* (2013.01); *C07K 2317/77* (2013.01); *C07K 2318/10* (2013.01); *C07K 2319/00* (2013.01); *C07K 2319/33* (2013.01)

(58) Field of Classification Search
None
See application file for complete search history.

(56) References Cited

U.S. PATENT DOCUMENTS

| 4,474,893 A | 10/1984 | Reading |
| 4,946,778 A | 8/1990 | Ladner et al. |
| 4,954,617 A | 9/1990 | Fanger et al. |
| 5,455,030 A | 10/1995 | Ladner et al. |
| 5,476,786 A | 12/1995 | Huston |
| 5,541,110 A | 7/1996 | Siegall |
| 5,545,807 A | 8/1996 | Surani et al. |
| 5,698,679 A | 12/1997 | Nemazee |
| 5,869,057 A | 2/1999 | Rock |
| 5,876,917 A | 3/1999 | Hart et al. |
| 5,922,845 A | 7/1999 | Deo et al. |
| 6,080,409 A | 6/2000 | Laus et al. |
| 6,117,977 A | 9/2000 | Lasky et al. |
| 6,277,959 B1 | 8/2001 | Valladeau et al. |
| 6,340,569 B1 | 1/2002 | Ball et al. |
| 6,432,666 B1 | 8/2002 | Hart et al. |
| 6,440,418 B1 | 8/2002 | Black et al. |
| 6,479,247 B1 | 11/2002 | Hart et al. |
| 6,756,478 B2 | 6/2004 | Valladeau et al. |
| 2002/0187131 A1 | 12/2002 | Hawiger et al. |
| 2003/0194391 A1 | 10/2003 | Ashman et al. |
| 2004/0001853 A1 | 1/2004 | George et al. |
| 2005/0037001 A1 | 2/2005 | Germeraad et al. |

FOREIGN PATENT DOCUMENTS

| WO | WO-86/01533 A1 | 3/1986 |
| WO | WO-88/00052 A1 | 1/1988 |
| WO | WO-92/03918 A1 | 3/1992 |
| WO | WO-92/07579 A1 | 5/1992 |
| WO | WO-93/04187 A1 | 3/1993 |
| WO | WO 93/12227 A1 | 6/1993 |
| WO | WO-94/10332 A1 | 5/1994 |
| WO | WO-95/15340 A1 | 6/1995 |
| WO | WO-96/23882 A1 | 8/1996 |
| WO | WO-97/45449 A1 | 12/1997 |
| WO | WO-98/15579 A1 | 4/1998 |
| WO | WO-98/24884 A1 | 6/1998 |
| WO | WO-99/02562 A1 | 1/1999 |
| WO | WO-99/16455 A1 | 4/1999 |
| WO | WO-99/24554 A2 | 5/1999 |
| WO | WO-99/47673 A2 | 9/1999 |
| WO | WO-99/55369 A1 | 11/1999 |
| WO | WO-99/58678 A2 | 11/1999 |
| WO | WO-00/00156 A2 | 1/2000 |
| WO | WO-00/00592 A1 | 1/2000 |
| WO | WO-00/18803 A2 | 4/2000 |
| WO | WO-00/63251 A1 | 10/2000 |
| WO | WO-01/25492 A1 | 4/2001 |
| WO | WO 01/85798 A2 | 11/2001 |

(Continued)

OTHER PUBLICATIONS

Kobayashi et al., Protein Engineering, vol. 12, No. 10. pp. 879-884, 1999.*
Janeway et al., Immunobiology, 6th Edition, 2004, Garland Science, p. 110-112.*
Casset et al. (2003) BBRC 307, 198-205.*
Cox et al., Vaccine, vol. 15, No. 3, 1997, p. 248-256.*
Apostolopoulos, Vasso et al, "Ex vivo targeting of the macrophage mannose receptor generates anti-tumor CTL responses," *Vaccine*, vol. 18:3174-3184 (2000).
Berard, Frederic et al, "Cross-Priming of Naive CD8 T Cells against Melanoma Antigens Using Dendritic Cells Loaded with Killed Allogeneic Melanoma Cells," *J. Exp. Med.*, vol. 192(11):1535-1543 (2000).

(Continued)

*Primary Examiner* — Yunsoo Kim
(74) *Attorney, Agent, or Firm* — Nelson Mullins Riley & Scarborough LLP; Jane E. Remillard, Esq.; Jill Gorny Sloper, Esq.

(57) ABSTRACT

The present invention provides novel antibody vaccine conjugates and methods of using the same to induce a cytotoxic T cell (CTL) response. In a particular, embodiment, the vaccine conjugate includes a human chorionic gonadotropin beta subunit (βhCG) antigen linked to an anti-mannose receptor (MR) antibody.

14 Claims, 12 Drawing Sheets

(56) References Cited

FOREIGN PATENT DOCUMENTS

| WO | WO-03/040169 A2 | 5/2003 |
|---|---|---|
| WO | WO-2004/026326 A2 | 4/2004 |

OTHER PUBLICATIONS

Berlyn, Kathleen A. et al, "Generation of CD4+ and CD8+ T Lymphocyte Responses by Dendritic Cells Armed with PSA/Anti-PSA (Antigen/Antibody) Complexes," *Clinical Immunology*, vol. 101(3):276-283 (2001).

Bird, Robert E. et al, "Single-Chain Antigen-Binding Proteins," *Science*, vol. 242(4877):423-426 (1988).

Brennan, Maureen et al, "Preparation of Bispecific Antibodies by Chemical Recombination of Monoclonal Immunoglobulin $G_1$ Fragments," *Science*, vol. 229:81-83 (1985).

Chien, Nadine C. et al, "Significant structural and functional change of an antigen-binding site by a distant amino acid substitution: Proposal of a structural mechanism," *Proc. Natl. Acad. Sci. USA*, vol. 86:5532-5536 (1989).

Frleta, Davor et al, "Class II-targeted antigen is superior to CD40-targeted antigen at stimulating humoral responses in vivo," *International Immunopharmacology*, vol. 1:265-275 (2001).

Galfre, G. et al, "Antibodies to major histocompatibility antigens produced by hybrid cell lines," *Nature*, vol. 266(7):550-552 (1977).

Geissmann, Frédéric et al, "A Subset of Human Dendritic Cells Expresses IgA Fc Receptor (CD89), Which Mediates Internalization and Activation Upon Cross-Linking by IgA Complexes," *The Journal of Immunology*, vol. 166:346-352 (2001).

Glennie, Martin J. et al "Preparation and Performance of Bispecific F(ab'γ)2 Antibody Containing Thioether-Linked Fab'γ Fragments," *The Journal of Immunology*, vol. 139(7):2367-2375 (1987).

Hawiger, Daniel et al, "Dendritic Cells Induce Peripheral T Cell Unresponsiveness Under Steady State Conditions In Vivo," *J. Exp. Med.*, vol. 194(6):769-779 (2001).

He, Li-Zhen et al, "A Novel Human Cancer Vaccine Elicits Cellular Responses to the Tumor-Associated Antigen, Human Chorionic Gonadotropin β," *Clinical Cancer Research*, vol. 10:1920-1927 (2004).

He, Lizhen et al, "An Antigen Presenting Cell-Targeted Cancer Vaccine that Elicits CD4 and CD8 Effector Responses to the hCGβ Tumor-Associated Antigen," *Proceedings of the American Association for Cancer Research*, vol. 44; 2nd ed., p. 167 (2003).

Karpovsky, Boris et al, "Production of Target-Specific Effector Cells Using Hetero-Cross-Linked Aggregates Containing Anti-Target Cell and Anti-Fcγ Receptor Antibodies," *Journal of Experimental Medicine*, vol. 160:1886-1701 (1984).

Kawakami, Yutaka et al, "The Use of Melanosomal Proteins in the Immunotherapy of Melanoma," *Journal of Immunotherapy*, vol. 21(4):237-246 (1998).

Kobayashi, Hiroyuki et al, "Tryptophan H33 plays an important role in pyrimidine (6-4) pyrimidone photoproduct binding by a high-affinity antibody," *Protein Engineering*, vol. 12(10):879-884 (1999).

Liu, Margaret A. et al, "Heteroantibody duplexes target cells for lysis by cytotoxic T lymphocytes," *Proc. Natl. Acad. Sci. USA*, vol. 82:8648-8652 (1985).

Lonberg, Nils et al, "Antigen-specific human antibodies from mice comprising four distinct modifications," *Nature*, vol. 368:856-859 (1994).

Monteiro, Renato C. et al, "Molecular Heterogeneity of Fcα Receptors Detected by Receptor-Specific Monoclonal Antibodies," *The Journal of Immunology*, vol. 148(6):1764-1770 (1992).

Noorman, Femke et al, "Monoclonal antibodies against the human mannose receptor as a specific marker in flow cytometry and immunohistochemistry for macrophages," *Journal of Leukocyte Biology*, vol. 61:63-72 (1997).

Nouri-Shirazi, Mahyar et al, "Dendritic Cells Capture Killed Tumor Cells and Present Their Antigens to Elicit Tumor-Specific Immune Response," *The Journal of Immunology*, vol. 165:3797-3803 (2000).

Paulus, H., "Preparation and Biomedical Applications of Bispecific Antibodies," *Behring Inst. Mitt.*, vol. 78:118-132 (1985).

Potter, Kathleen N. et al, "Evidence for Involvement of a Hydrophobic Patch in Framework Region 1 of Human V4-34-Encoded Igs in Recognition of the Red Blood Cell I Antigen," *The Journal of Immunology*, vol. 169:3777-3782 (2002).

Ramakrishna, Vanky et al, "Mannose Receptor Targeting of Tumor Antigen pmel17 to Human Dendritic Cells Directs Anti-Melanoma T Cell Responses via Multiple HLA Molecules," *The Journal of Immunology*, vol. 172:2845-2852 (2004).

Rudikoff, Stuart et al, "Single amino acid substitution altering antigen-binding specificity," *Proc. Natl. Acad. Sci. USA*, vol. 79:1979-1983 (1982).

Sallusto, Federica et al, "Dendritic Cells Use Macropinocytosis and the Mannose Receptor to Concentrate Macromolecules in the Major Histocompatibility Complex Class II Compartment: Downregulation by Cytokines and Bacterial Products," *J. Exp. Med.*, vol. 182:389-400 (1995).

Tempest, Philip R. et al, "A Humanized Anti-Tumor Necrosis Factor-α Monoclonal Antibody That Acts as a Partial, Competitive Antagonist of the Template Antibody," *Hybridoma*, vol. 13(3):183-190 (1994).

Tjoa, Benjamin A. et al, "Development of dendritic-cell based prostate cancer vaccine," *Immunology Letters*, vol. 74:87-93 (2000).

Tüting, Thomas et al, "Autologous Human Monocyte-Derived Dendritic Cells Genetically Modified to Express Melanoma Antigens Elicit Primary Cytotoxic T Cell Responses In Vitro: Enhancement by Cotransfection of Genes Encoding the Th1-Biasing Cytokines IL-12 and IFN-α," *The Journal of Immunotherapy*, vol. 160:1139-1147 (1998).

Wallace, Paul K. et al, "Exogenous antigen targeted to FcγRI on Myeloid cells is presented in association with MHC class I," *Journal of Immunological Methods*, vol. 248:183-194 (2001).

Wang, Hui et al, "Rapid antibody responses by low-dose, single-step, dendritic cell-targeted immunization," *PNAS*, vol. 96(2):847-852 (2000).

Ward, E. Sally et al, "Binding activities of a repertoire of single immunoglobulin variable domains secreted from *Escherichia coli*," *Nature*, vol. 341:544-546 (1989).

You, Zhaoyang et al, "Targeting Dendritic Cells to Enhance DNA Vaccine Potency," *Cancer Research*, vol. 61:3704-3711 (2001).

Austyn, Jonathan M. et al., "Isolation and Characterization of Dendritic Cells from Mouse Heart and Kidney," *Journal of Immunology*, vol. 152:2401-2410 (1994).

Bonifaz, Laura et al., "Efficient Targeting of Protein Antigen to the Dendritic Cell Receptor D-205 in the Steady State Leads to Antigen Presentation on Major Histocompatibility Complex Case I Products and Peripheral CD8+ T Cell Tolerance," *J. Exp. Med.*, vol. 196(12):1627-1938 (2002).

Breel, M. et al., "Subpopulations of lymphoid and non-lymphoid cells in bronchus-associated lymphoid tissue (BALT) of the mouse," *Immunology*, vol. 63:657-662 (1988).

Chen, Wen-Ji et al., "NPXY, a Sequence Often Found in Cytoplasmic Tails, Is Required for Coated Pit-mediated Internalization of the Low Density Lipoprotein Receptor," *The Journal of Biological Chemistry*, vol. 265(6):3116-3123 (1990).

Chen, Yvonne et al., "Selection and Analysis of an Optimized Anti-VEGF Antibody: Crystal Strucutre of an Affinity-matured Fab in Complex with Antigen," *J. Mol. Biol.*, vol. 293:865-881 (1999).

Collawn, James F. et al., "Transferrin Receptor Internalization Sequence YXRF Implicates a Tight Turn as the Structural Recognition Motif for Endocytosis," *Cell*, vol. 63:1061-1072 (1990).

De Maagd, R.A. et al., "The human thymus microenvironment: heterogeneity detected by monoclonal anti-epithelial cell antibodies," Immunology, vol. 54:745-754 (1985).

De Pascalis, Roberto et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, vol. 169:3076-3084 (2002).

Drickamer, K. et al., "Biology of animal lectins," Annu. Rev. Cell Biol., vol. 9:237-264 (1993).

(56) References Cited

OTHER PUBLICATIONS

Ezekowitz, R. Alan B. et al., "Molecular Characterization of the Human Macrophage Mannose Receptor: Demonstration of Multiple Carbohydrate Recognition-like Domains and Phagocytosis of Yeasts in Cos-1 Cells," J. Exp. Med., vol. 172:1785-1794 (1990).

Guo, Ming et al., "A Monoclonal Antibody to the DEC-205 Endocytosis Receptor on Human Dendritic Cells," *Human Immunology*, vol. 61:729-738 (2000).

Inaba, Kayo et al., "Tissue Distribution of the DEC-205 Protein That is Detected by the Monoclonal Antibody NLDC-145, I. Expression on Dendritic Cells and Other Subsets of Mouse Leukocytes," *Cellular Immunology*, vol. 163:148-156 (1995).

Ishizaki, Jun et al., "Molecular Cloning of Pancreatic Group I Phospholipase $A_2$ Receptor," *The Journal of Biological Chemistry*, vol. 269(8):5897-5904 (1994).

Jiang, Wanping et al., "The receptor DEC-205 expressed by dendritic cells and thymic epithelial cells is involved in antigen processing," *Nature*, vol. 375:151-155 (1995).

Kraal, Georg et al., "Langerhans' Cells, Veiled Cells, and Interdigitating Cells in the Mouse Recognized by a Monoclonal Antibody," J. Exp. Med., vol. 163:981-997 (1986).

Lambeau, Gérard et al., "Cloning and Expression of a Membrane Receptor for Secretory Phospholipases A2," The Journal of Biological Chemistry, vol. 269(3):1575-1578 (1994).

Lamminmäki, Urpo et al., "Crystal Structure of a Recombinant Anti-estradiol Fab Fragment in Complex with 17β-Estradiol," The Journal of Biological Chemistry, vol. 276(39):36687-36694 (2001).

Lu, Lina et al., "Propagation of Dendritic Cell Progenitors from Normal Mouse Liver Using Granulocyte/Macrophage Colony-stimulating Factor and Their Maturational Development in the Presence of Type-1 Collagen," J. Exp. Med., vol. 179:1823-1834 (1994).

MacCallum, Robert M. et al., "Antibody-antigen Interactions: Contact Analysis and Binding Site Topography," J. Mol. Biol., vol. 262:732-745 (1996).

McKay, Paul F. et al., "The gp200-MR6 molecule which is functionally associated with the IL-4 receptor modulates B cell phenotype and is a novel member of the human macrophage mannose receptor family," Eur. J. Immunol., vol. 28:4071-4083 (1998).

McKown, Kevin M. et al., "Lack of Efficacy of Oral Bovine Type II Collagen Added to Existing Therapy in Rheumatoid Arthritis," Arthritis & Rheumatism, vol. 42 (6):1204-1208 (1999).

Mestas, Javier et al., "Of Mice and Not Men: Differences between Mouse and Human Immunology," *The Journal of Immunology*, vol. 172:2731-2738 (2004).

Nossal, "Immunologic Tolerance," Fundamentals of Immunology, 2nd Edition, Paven Press Ltd., W.E. Paul (Ed.), Chpt. 19, pp. 571-586 (1989).

Puré, Ellen et al., "Antigen Processing by Epidermal Langerhans Cells Correlates with the Level of Biosynthesis of Major Histocompatibility Complex Class II Molecules and Expression of Invariant Chain," *J. Exp. Med.*, vol. 172:1459-1469 (1990).

Ramakrishna, Venky et al, "Synergistic Role of TLR Agonists in T Cell-Mediated Immunity Induced by Mannose Receptor Antibody Targeting of Tumor Antigens to Human DCs," J. Immunother., vol. 28(6):658 (2005).

Schjetne, Karoline W. et al., "Delivery of Antigen to CD40 Induces Protective Immune Responses against Tumors," The Journal of Immunology, vol. 178:4169-4176 (2007).

Spack, E.G., "Antigen-specific therapies for the treatment of multiple sclerosis: a clinical trial update," Expert Opin. Investig. Drugs, vol. 6(11):1715-1727 (1997).

Steinman, Ralph M., "The Dendritic Cell System and Its Role in Immunogenicity," Annu. Rev. Immunol., vol. 9:271-296 (1991).

Swiggard, William J. et al., "DEC-205, a 205-kDa Protein Abundant on Mouse Dendritic Cells and Thymic Epithelium That is Detected by the Monoclonal Antibody NLDC-145: Purification, Characterization, and N-Terminal Amino Acid Sequence," Cellular Immunology, vol. 165:302-311 (1995).

Taylor, Lisa D. et al., "A transgenic mouse that expresses a diversity of human sequence heavy and light chain immunoglobulins," Nucleic Acids Research, vol. 20(23):6287-6295 (1992).

Taylor, Maureen E. et al., "Contribution to Ligand Binding by Multiple Carbohydrate-recognition Domains in the Macrophage Mannose Receptor," The Journal of Biological Chemistry, vol. 267(3):1719-1726 (1992).

Taylor, Maureen E. et al., "Structural Requirements for High Affinity Binding of Complex Ligands by the Macrophage Mannose Receptor," *The Journal of Biological Chemistry*, vol. 268(1):399-404 (1993).

Tufveson, G. et al., "New Immunosuppressants: Testing and Development in Animal Models and the Clinic: with Special Reference to DSG," *Immunological Reviews*, vol. 136(1):99-109 (1993).

Steinman, Ralph M., "Dendritic cells and immune-based therapies," *Experimental Hematology*, vol. 24:859-862 (1996).

Tan, M.C. Agnes A. et al., "Mannose receptor-mediated uptake of antigens strongly enhances HLA class II-restricted antigen presentation by cultured dendritic cells," Eur. J. Immunol., vol. 27:2426-2435 (1997).

Faulkner, Lee et al., "IL-2 linked to a peptide from influenza hemagglutinin enhances T cell activation by affecting the antigen-presentation function of bone marrow-derived dendritic cells," International Immunology, vol. 13(6):713-721 (2001).

Invitation to Pay Additional Fees for Application No. PCT/US2008/082745, dated Feb. 12, 2009.

Dangles, Virginie et al., "Tumor-associated antigen human chorionic gonadotropin beta contains numerous antigenic determinants recognized by in vitro-induced CD8+ and CD4+ T lymphocytes," Cancer Immunol. Immunother., vol. 50:673-681 (2002).

\* cited by examiner

Anti-Mannose Receptor B11 VH

V-segment: Locus - 5-51  Name: DP-73/V5-51
    D-segment: Unknown
    J-segment: JH4b

```
         E   V   Q   L   V   Q   S   G   A   E   V   K   K   P   G   E   S   L
  1     GAG GTG CAG CTG GTG CAG TCT GGA GCA GAG GTG AAA AAG CCC GGG GAG TCT CTG

CDR 1
                                                                ------------------
         R   I   S   C   K   G   S   G   D   S   F   T   T   Y   W   I   G   W
 55     AGG ATC TCC TGT AAG GGT TCT GGA GAC AGT TTT ACC ACC TAC TGG ATC GGC TGG

CDR 2
                                                                ------------------
         V   R   Q   M   P   G   K   G   L   E   W   M   G   I   I   Y   P   G
109     GTG CGC CAG ATG CCC GGG AAA GGC CTG GAG TGG ATG GGG ATC ATC TAT CCT GGT

CDR 2
        ------------------------------------------------
         D   S   D   T   I   Y   S   P   S   F   Q   G   Q   V   T   I   S   A
163     GAC TCT GAT ACC ATA TAC AGC CCG TCC TTC CAA GGC CAG GTC ACC ATC TCA GCC

D   K   S   I   S   T   A   Y   L   Q   W   S   S   L   K   A   S   D
217     GAC AAG TCC ATC AGC ACC GCC TAC CTG CAG TGG AGC AGC CTG AAG GCC TCG GAC

CDR 3
                                                    ------------------------------
         T   A   M   Y   Y   C   T   R   G   D   R   G   V   D   Y   W   G   Q
271     ACC GCC ATG TAT TAC TGT ACG AGA GGG GAC CGG GGC GTT GAC TAC TGG GGC CAG
                                                    ↳ JH4b

G   T   L   V   T   V   S   S
325     GGA ACC CTG GTC ACC GTC TCC TCA
```

*Fig. 8*

Anti-Mannose Receptor B11 VL

V-segment: Locus - L15       Name: DPK7/HK134
    J-segment: JK1

```
          D   I   Q   M   T   Q   S   P   S   S   L   S   A   S   V   G   D   R
   1      GAC ATC CAG ATG ACC CAG TCT CCA TCC TCA CTG TCT GCA TCT GTA GGA GAC AGA

CDR 1
                                 ------------------------------------------------
          V   T   I   T   C   R   A   S   Q   G   I   S   R   W   L   A   W   Y
  55      GTC ACC ATC ACT TGT CGG GCG AGT CAG GGT ATT AGC AGG TGG TTA GCC TGG TAT

CDR 2
                                                              ------------------
          Q   Q   K   P   E   K   A   P   K   S   L   I   Y   A   A   S   S   L
 109      CAG CAG AAA CCA GAG AAA GCC CCT AAG TCC CTG ATC TAT GCT GCA TCC AGT TTG

CDR 2
          --------
          Q   S   G   V   P   S   R   F   S   G   S   G   S   G   T   D   F   T
 163      CAA AGT GGG GTC CCA TCA AGG TTC AGC GGC AGT GGA TCT GGG ACA GAT TTC ACT

CDR 3
                                                                      ----------
          L   T   I   S   G   L   Q   P   E   D   F   A   T   Y   Y   C   Q   Q
 217      CTC ACC ATC AGC GGC CTG CAG CCT GAA GAT TTT GCA ACT TAT TAC TGC CAA CAG

CDR 3
          ------------------------------
          Y   N   S   Y   P   R   T   F   G   Q   G   T   K   V   E   I   K
 271      TAT AAT AGT TAC CCT CGG ACG TTC GGC CAA GGG ACC AAG GTG AAA ATC AAA
                                   ↳ JK 1
```

*Fig. 9*

Anti-Mannose Receptor VH5-51 Regions

```
                                                          CDR1
5-51 germline   E V Q L V Q S G A E V K K P G E S L K I S C K G S G Y S F T S Y W I G
B11             - - - - - - - - - - - - - - - - - R - - - - - - - - D - - T - - - -

CDR2
5-51 germline   W V R Q M P G K G L E W M G I I Y P G D S D T R Y S P S F Q G Q V T I
B11             - - - - - - - - - - - - - - - I - - - - - - - - - - - - - - - - - -

5-51 germline   S A D K S I S T A Y L Q W S S L K A S D T A M Y Y C A R
B11             - - - - - - - - - - - - - - - - - - - - - - - - - - -    CDR3
                                                                       - T - G D R G V D Y 5-51 germline   W G Q G T L V T V S S
B11
```

*Fig. 12*

Anti-Mannose Receptor VH regions (VH5-51):

```
VH5-51
Germline:     GAG GTG CAG CTG GTG CAG TCT GGA GCA GAG GTG AAA AAG CCC GGG GAG TCT CTG AAG ATC TCC TGT AAG GGT
B11:          --- --- --- --- --- --- --- --- --- --- --- --- --- --- --- --- --- --- -G- --- --- --- --- ---
                                                                      CDR1
V germline:   TCT GGA TAC AGC TTT ACC AGC TAC TGG ATC GGC TGG GTG CGC CAG ATG CCC GGG AAA GGC CTG GAG TGG ATG
B11:          --- --- G-- --T --- --- -C- --- --- --- --- --- --- --- --- --- --- --- --- --- --- --- --- ---
                                                                      CDR2
V germline:   GGG ATC ATC TAT CCT GGT GAC TCT GAT ACC AGA TAC AGC CCG TCC TTC CAA GGC CAG GTC ACC ATC TCA GCC
B11:          --- --- --- --- --- --- --- --- --- --- -T- --- --- --- --- --- --- --- --- --- --- --- --- ---

V germline:   GAC AAG TCC ATC ACC AGC ACC GCC TAC CTG CAG TGG AGC AGC CTG AAG GCC TCG GAC ACC GCC ATG TAT TAC TGT
B11:          --- --- --- --- --- --- --- --- --- --- --- --- --- --- --- --- --- --- --- --- --- --- --- --- ---
                                                 CDR3
V germline:   GCG AGA      GGG GAC CGG GGC GTT GAC TAC TGG GGC CAG GGA ACC CTG GTC ACC GTC TCC TCA
B11:          A-- ---      --- --- --- --- --- --- --- --- --- --- --- --- --- --- --- --- ---
```

Fig. 13

Anti-Mannose Receptor Vk L15 Regions

```
                                              CDR1
L15 germline  D I Q M T Q S P S S L S A S V G D R V T I T C R A S Q G I S S W L A W Y Q
B11           - - - - - - - - - - - - - - - - - - - - - - - - - - - - - R - - - - - -

CDR2
L15 germline  Q K P E K A P K S L I Y A A S S L Q S G V P S R F S G S G S G T D F T L T
B11           - - - - - - - - - - - - - - - - - - - - - - - - - - - - - - - - - - -

CDR3
L15 germline  I S S L Q P E D F A T Y Y C Q Q Y N S Y P - - R T F G Q G T K V E I K
B11           - - G - - - - - - - - - - - - - - - - - - - -
```

Fig. 14

Anti-Mannose Receptor VK Regions

```
L15 germline: GAC ATC CAG ATG ACC CAG TCT CCA TCC TCA CTG TCT GCA TCT GTA GGA GAC AGA GTC ACC ATC
B11:          --- --- --- --- --- --- --- --- --- --- --- --- --- --- --- --- --- --- --- --- ---

CDR1
L15 germline: ACT TGT CGG GCG AGT CAG GGT ATT AGC AGC TGG TTA GCC TGG TAT CAG CAG AAA CCA GAG AAA
B11:          --- --- --- --- --- --- --- --- --G --- --- --- --- --- --- --- --- --- --- --- ---

CDR2
L15 germline: GCC CCT AAG TCC CTG ATC TAT GCT GCA TCC AGT TTG CAA AGT GGG GTC CCA TCA AGG TTC AGC
B11:          --- --- --- --- --- --- --- --- --- --- --- --- --- --- --- --- --- --- --- --- ---

L15 germline: GGC AGT GGA TCT GGG ACA GAT TTC ACT CTC ACC ATC AGC AGC CTG GAG CCT GAA GAT TTT GCA
B11:          --- --- --- --- --- --- --- --- --- --- --- --- --- --- G-- --- --- --- --- --- ---

CDR3
L15 germline: ACT TAT TAC TGC CAA CAG TAT AAT AGT TAC CCT         CGG ACG TTC GGC CAA GGG ACC AAG GTG GAA
B11:          --- --- --- --- --- --- --- --- --- --- ---         --- --- --- --- --- --- --- --- --- ---

B11:          ATC AAA
```

Fig. 15

ANTIBODY VACCINE CONJUGATES AND USES THEREFOR

BACKGROUND OF THE INVENTION

The immune response is initiated at the level of professional antigen presenting cells (APC), which include dendritic cells (DC) and macrophages (Mg), that reside in tissues throughout the body. DCs express high levels of cell surface molecules and complementary receptors that interact with T lymphocytes and, therefore, induce potent immune responses. DCs also secrete cytokines, chemokines and proteases which initiate immune responses and culminate in the amplification of both cellular and humoral immunity.

DCs express on their surface major histocompatibility complex (MHC) molecules that bind fragments of antigens. T cells which express T cell receptors (TCR) that recognize such antigen-MHC complexes become activated and initiate the immune cascade. In general, there are two types of MHC molecules, MHC class I and MHC class II molecules. MHC class I molecules present antigen to specific $CD8^+$ T cells and MHC class II molecules present antigen to specific $CD4^+$ T cells.

For effective treatment of many diseases, particularly cancers, vaccines must elicit a potent cytotoxic T lymphocyte (CTL) response, also referred to as a cytotoxic T cell response. Cytotoxic T cells predominantly include $CD8^+$ T cells which recognize antigen in the context of MHC class I. The processing of antigens in the context of MHC class I molecules differs significantly from that of MHC class II molecules. Antigens delivered exogenously to APCs are processed primarily for association with MHC class II molecules. In contrast, due to the intracellular location of MHC class I molecules, antigens delivered endogenously to APCs are processed primarily for association with MHC class I molecules. This is not only true for APCs, as all nucleated cells express MHC class I molecules, and are continuously displaying on their surface endogenously produced antigens in association with MHC class I molecules.

For this reason, cells infected with virus or tumor cells expressing unique proteins can be targeted by CTLs when viral or tumor antigens are displayed as a peptide bound to MHC class I molecules. However, DCs, under specific conditions, have the unique capacity also to allow exogenous antigens access to internal compartments for binding to MHC class I molecules, so that they are presented to T cells via both MHC class I and class II pathways. This process is called cross-priming or cross-presentation.

Accordingly, while antibody-mediated responses have demonstrated impressive protective or therapeutic efficacy for specific diseases when directed against particular secreted or cell surface antigens, the most effective immunotherapy for many diseases appears to require T cell-mediated immune responses, particularly CTL responses. Since effective CTL responses are not limited to extracellular antigens, there exist possibilities for developing antigen-based therapeutic vaccines that are not effective antibody targets. Therefore, new methods for generating CTLs in response to disease-associated antigens have been of great interest, as these cells are thought to be critical for the efficacy of many vaccines in general, and essential to most therapeutic cancer vaccines.

One vaccine approach which has been tested to date employs immunizing with antigenic peptides. This method of immunization bypasses the need for antigen uptake and processing and relies on the ability of the peptide to bind directly to MHC class I molecules already expressed on the surface of the APC. Although this method has clearly shown evidence of CTL induction in patients, the method has several limitations. The antigenic peptide must be pre-established, different peptides are required for individuals with different MHC haplotypes, and peptides are short-lived in vivo.

Another approach which has been tested employs antibody-antigen complexes. Paul et al. (62) showed that antibodies specific for a given antigen could enhance humoral immune responses against the antigen in mice, presumably by delivering the immune complexes to Fc receptors for IgG (FcγR) expressed on APCs. Wernersson and colleagues (63) studied the role of individual FcγRs in the enhancement of immune responses using immune complexes in vivo. Their studies demonstrated that FcγRI is sufficient to mediate enhanced immune responses. However, such immune complexes do not target APCs specifically, as they also bind to Fc receptors on many cells that are not involved in antigen presentation, thereby, decreasing the efficiency of antigen delivery.

Subsequent studies have used antibodies to selectively target antigens to a variety of receptors on APCs, and have demonstrated that such selective delivery is capable of inducing humoral responses (66, 67). In addition, it has been shown that immune complexes bound to FcR on DCs are processed and presented in context of MHC class I (64, 65). Moreover, many such FcR-targeting approaches are limited because FcR are expressed on many non-APC such as platelets and neutrophils. Ideally, a vaccine that targets APC specifically and is capable of inducing an effective MHC class I-restricted CTL response, as well as an effective MHC class II—restricted TH response could offer improved efficacy in treating certain diseases.

Similarly, mannosylated antigens have been shown to induce humoral immune responses and T cell-mediated immune responses, such as CTL responses. However, mannosylated antigens do not target APC specifically due to the significant abundance of other mannose binding proteins. Furthermore, mannosylated proteins are internalized by immature DCs through macropinocytic mechanisms. Therefore, the mechanisms and nature of immune responses generated by mannosylation of antigens differs greatly from that generated by specific targeting of antigens to mannose receptors using antibodies.

Since current methods do not efficiently and specifically target APCs, many therapeutic vaccines require the purification of DC from patients, which are reinfused after exposure to the antigen.

Accordingly, the need exists for improved vaccines capable of efficiently targeting APCs and generating antigen-specific T cell-mediated immune responses, including antigen-specific CTL responses, required for effective treatment of many diseases.

SUMMARY OF THE INVENTION

The present invention provides antibody-based vaccines and methods for generating antigen-specific T cell-mediated immune responses required for effective treatment of many diseases. In particular, a potent antigen-specific cytotoxic T lymphocyte (CTL) response is induced by targeting one or more protein antigens to antigen presenting cells (APCs), using antibodies which bind to particular receptors expressed on APCs. Preferred receptors include C-lectins, particularly the human mannose receptor, which are expressed on both dendritic cells (DCs) and macrophages. As demonstrated by way of the present invention, targeting the mannose receptor using antibody-antigen conjugates results in processing of the antigen through both MHC class I and class II pathways.

Thus, antigen-specific CTLs (e.g., CD8+ T cells) are induced, as well as other important effector T cells, including helper T cells (e.g., CD4+ T cells).

Accordingly, in one aspect, the present invention provides a method for inducing or enhancing a CTL response against an antigen by forming a conjugate of the antigen and a monoclonal antibody which binds to a human APC, e.g., a monoclonal antibody which binds to the human mannose receptor expressed on human APC. The conjugate is then contacted, either in vivo or ex vivo, with APCs such that the antigen is internalized, processed and presented to T cells in a manner which induces or enhances a CTL response (e.g., a response mediated by CD8+ cytotoxic T cells) against the antigen. In a preferred embodiment, this serves also to induce a helper T cell response (e.g., a response mediated by CD4+ helper T cells) against the antigen. Thus, the immune response is induced through both MHC class I and MHC class II pathways. The APCs can also be contacted with an adjuvant or an immunostimulatory agent, such as a cytokine, which stimulates proliferation of dendritic cells to further enhance the immune response. Such agents can be contacted separately from the molecular conjugate or linked to the molecular conjugate.

Accordingly, in a particular embodiment, the invention provides a vaccine conjugate comprising a monoclonal antibody which binds to a human APC linked to an antigen and to an immunostimulatory agent. The immunostimulatory agent can be linked to the conjugate either covalently or non-covalently. Alternatively, the immunostimulatory agent can be genetically fused to the conjugate (e.g., expressed together with the conjugate as a single fusion protein). A variety of suitable immunostimulatory agents can be employed including, but not limited to: CD40 ligand; cytokines, such as IFN-$\alpha$, IFN-$\beta$, IFN-$\gamma$ and IL-2; colony-stimulating factors, such as G-CSF (granulocyte colony-stimulating factor) and GM-CSF (granulocyte-macrophage colony-stimulating factor); an anti-CTLA-4 antibody; toll receptor agonists (e.g., flagellin and MALP-2 (macrophage activating lipopeptide-2); LPS (endotoxin); R837 (3M Pharmaceuticals, St. Paul, Minn.); R848 (3M Pharmaceuticals, St. Paul, Minn.); polyI:C (inosine:cytosine polynucleotide); ssRNA; dsRNA; Bacille Calmette-Guerin (BCG); Levamisole hydrochloride; and intravenous immune globulins.

A variety of suitable antibodies can be employed in the conjugates of the present invention including, but not limited to those derived from any species (e.g., human, murine, rabbit etc.) and/or those engineered and expressed recombinantly (e.g., chimeric, humanized and human antibodies). Preferred antibodies include human monoclonal antibodies. Antibodies used in the invention also can include any antibody isotype, such as IgG1, IgG2, IgG3, IgG4, IgM, IgA1, IgA2, IgAsec, IgD, or IgE, although preferred antibodies are of the IgG isotype. The antibodies can be whole antibodies or antigen-binding fragments thereof including, for example, Fab, F(ab')$_2$, Fv and single chain Fv fragments.

Preferred antibodies for use in the present invention include human monoclonal antibodies that bind to the human mannose receptor. In one embodiment, the antibody is encoded by human heavy chain and human kappa light chain nucleic acids comprising nucleotide sequences in their variable regions as set forth in SEQ ID NO:3 and SEQ ID NO:7, respectively, or a nucleotide sequence that is sufficiently homologous to SEQ ID NO:3 or SEQ ID NO:7 such that the antibody retains the ability to bind to dendritic cells.

Still other preferred human antibodies include those characterized as binding to the human mannose receptor and having a human heavy chain and human kappa light chain variable regions comprising the amino acid sequences as set forth in SEQ ID NO:4 and SEQ ID NO:8, respectively, or an amino acid sequence that is sufficiently homologous to SEQ ID NO:4 or SEQ ID NO:8 such that the antibody retains the ability to bind to dendritic cells.

Still other particular human antibodies of the invention include those which comprise a complementarity determining region (CDR) domain having a human heavy and light chain CDR1 region, a human heavy and light chain CDR2 region, and a human heavy and light chain CDR3 region, wherein (a) the CDR1, CDR2, and CDR3 of the human heavy chain regions comprise an amino acid sequence selected from the group consisting of the amino acid sequences of the CDR1, CDR2, and CDR3 regions shown in FIG. 8 (SEQ ID NOs:13, 14, or 15), and conservative sequence modifications thereof, and (b) the CDR1, CDR2, and CDR3 of the human light chain regions comprise an amino acid sequence selected from the group consisting of the amino acid sequences of the CDR1, CDR2, and CDR3 regions shown in FIG. 9 (SEQ ID NOs:16, 17, or 18), and conservative sequence modifications thereof.

Antibodies derived from a particular gemmline sequence, for example, antibodies obtained from a system using human immunoglobulin sequences, e.g., by immunizing a transgenic mouse carrying human immunoglobulin genes or by screening a human immunoglobulin gene library, are also included in the present invention.

Human antibodies for use in the invention can be produced recombinantly in a host cell, such as a transfectoma (e.g., a transfectoma consisting of immortalized CHO cells or lymphocytic cells) containing nucleic acids encoding the heavy and light chains of the antibody, or be obtained directly from a hybridoma which expresses the antibody (e.g., which includes a B cell obtained from a transgenic nonhuman animal, e.g., a transgenic mouse, having a genome comprising a human heavy chain transgene and a human light chain transgene that encode the antibody, fused to an immortalized cell). In a particular embodiment, the antibodies are produced by a hybridoma, or by a host cell (e.g., a CHO cell) transfectoma containing human heavy chain and human light chain nucleic acids which comprise nucleotide sequences SEQ ID NOs:3 and 7, respectively, and conservative modifications thereof.

Suitable antigens for use in the present invention include any antigen, or antigenic portion thereof, against which a protective or therapeutic immune responses is desired including, for example, a variety of tumor and infectious disease antigens. Particular antigens can be selected from, among others, human chorionic gonadotropin beta subunit ($\beta$hCG), Gp100, prostate associated antigen (PSA), Pmel-17, colon, lung, pancreas, breast, ovary, and germ cell derived tumor cell antigens, viral proteins, bacterial proteins, carbohydrates, and fungal proteins. In accordance with the invention, such antigens are linked to antibodies to form highly effective antibody vaccine conjugates.

In another aspect, the present invention provides a particular antibody vaccine conjugate that includes $\beta$hCG linked to an antibody which binds to the human mannose receptor. In one embodiment, the conjugate comprises a human heavy chain which is linked to $\beta$hCG, such as the B11-$\beta$hCG conjugate described herein having a heavy chain comprising the amino acid sequence shown in SEQ ID NO:10. A single chain version of the B11-$\beta$hCG conjugate is also provided, comprising the amino acid sequence shown in SEQ ID NO:12.

The present invention further provides compositions (e.g., pharmaceutical compositions) containing one or more antibody vaccine conjugates of the invention. The compositions can additionally include one or more adjuvants or other agents known to enhance immune responses and/or increase the activity of APCs.

Other features and advantages of the instant invention will be apparent from the following detailed description and claims.

BRIEF DESCRIPTION OF THE DRAWINGS

FIG. 8 shows the nucleotide sequence (SEQ ID NO:3) and corresponding amino acid sequence (SEQ ID NO:4) of the heavy chain V region of human monoclonal antibody B11 with CDR regions designated (SEQ ID NOs: 13, 14, and 15).

FIG. 9 shows the nucleotide sequence (SEQ ID NO:7) and corresponding amino acid sequence (SEQ ID NO:8) of the light (kappa) chain V region of human monoclonal antibody B11 with CDR regions designated (SEQ ID NOs: 16, 17, and 18).

FIG. 12 shows the amino acid sequence (SEQ ID NO:4) of the heavy chain V region of human monoclonal antibody B11 compared to the germline sequence (SEQ ID NO:30), VH5-51 germline.

FIG. 13 shows the nucleotide sequence (SEQ ID NO:3) of the heavy chain V region of human monoclonal antibody B11 compared to the germline sequence (SEQ ID NO:29), VH5-51 germline.

FIG. 14 shows the amino acid sequence (SEQ ID NO:8) of the light (kappa) chain V region of human monoclonal antibody B11 with CDR regions designated compared to the germline sequence (SEQ ID NO:32), Vk-L15 germline.

FIG. 15 shows the nucleotide sequence (SEQ ID NO:7) of the light (kappa) chain V region of human monoclonal antibody B11 with CDR regions designated compared to the germline sequence (SEQ ID NO:31), Vk-L15 germline.

DETAILED DESCRIPTION OF THE INVENTION

Figure 1:
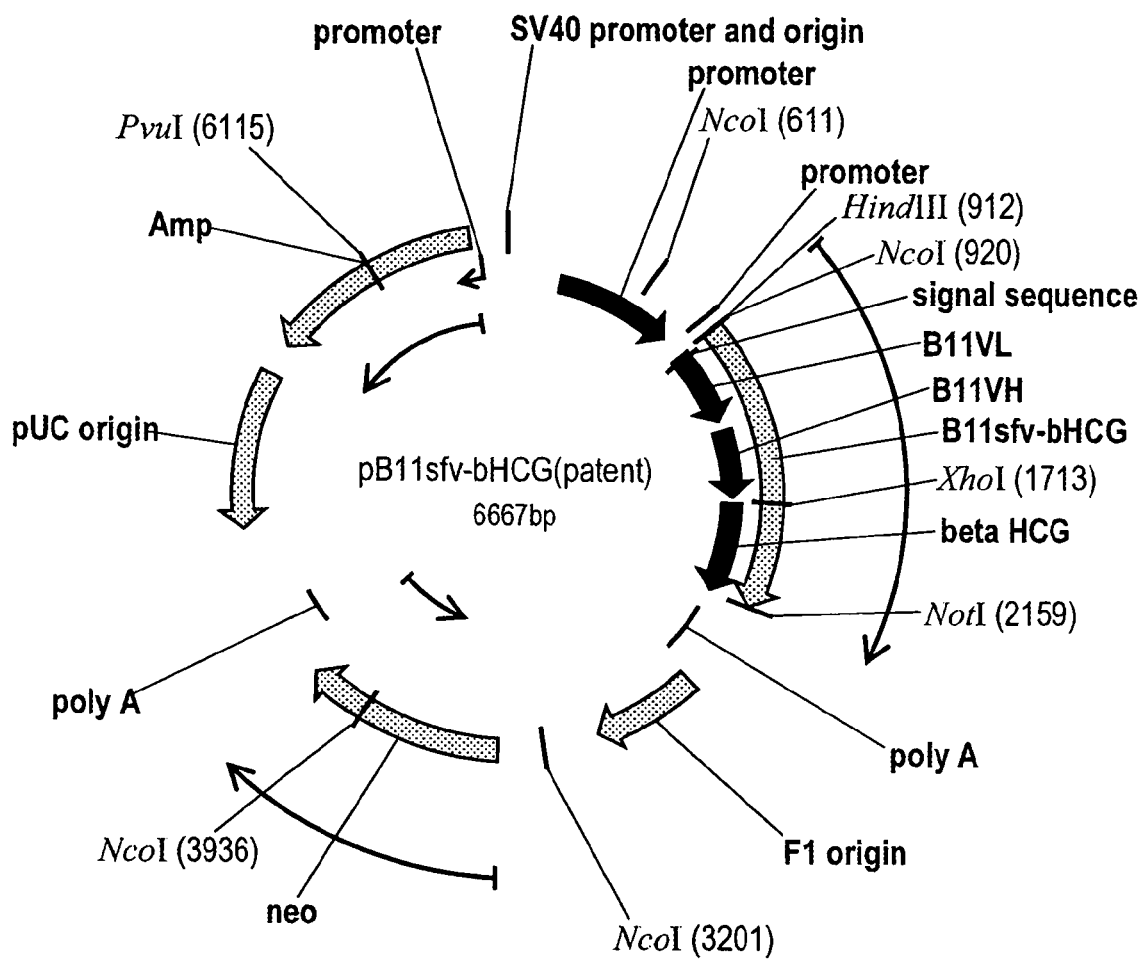
FIG. 1 shows a map of the molecular conjugate (SEQ ID NOs:11 and 12) encoding a fusion protein containing the single chain B11 antibody linked to βhCG antigen (pB11sfv-βhCG).

The present invention is based on the discovery that important T cell-mediated immune responses can be generated by targeting antigens to antigen presenting cells (APCs) using antibodies directed against particular cellular receptors. Specifically, for effective treatment of many diseases, such as cancers and infectious diseases, vaccines must elicit a potent antigen-specific cytotoxic T lymphocyte (CTL) response, primarily mediated by CD8+ T cells which recognize antigen in the context of MHC class I. For optimal immunization, this is preferably accompanied by other important effector T cell functions, including induction of antigen-specific helper T cells, such as CD4+ T cells, which recognize antigen in the context of the MHC class II pathway. Thus, effective vaccines should induce antigen-specific CTLs, preferably in combination with other T cell-mediated immune responses, through multiple MHC pathways.

Accordingly, the present invention provides novel antibody-based vaccine conjugates and methods for inducing or enhancing antigen-specific cytotoxic T cell (CTL) responses. Therapies of the invention employ molecular conjugates comprising antibodies which bind to antigen presenting cells (APC), such as dendritic cells (DC) and macrophages, linked to an antigen. The molecular conjugates can be administered alone or with other immunostimulatory agents and/or adjuvants that further enhance the immune response against the antigen. In one embodiment, the immunostimulatory agent is co-administered with the molecular conjugate. In another embodiment, the immunostimulatory agent is administered prior to or after administration of the molecular conjugate. In yet another embodiment, the immunostimulatory agent is linked (e.g., covalently, non-covalently or recombinantly) to the molecular conjugate. For example, the immunostimulatory agent can be genetically fused or chemically linked to the molecular conjugate via, e.g., the heavy and/or light chain of the antibody portion of the conjugate.

Antibodies which target APCs are known in the art and include, for example, antibodies which target Class I or Class II major histocompatibility (MHC) determinants on APC (78, 79, 81, 83). Other antibodies include those which target Fc receptors on APCs (77, 79, 80, 81, 82, 83), as well as surface immunoglobulins on B cells (84).

In a particular embodiment exemplified herein, the molecular conjugate includes an antibody which binds to the mannose receptor (MR) on human DCs, linked to the βhCG antigen. Such conjugates can be contacted with APCs either in vivo or ex vivo to generate desired CTL responses.

In order that the present invention may be more readily understood, certain terms are first defined. Additional definitions are set forth throughout the detailed description.

As used herein, the term “antigen presenting cell (APC)” refers to a class of immune cells capable of internalizing and processing an antigen, so that antigenic determinants are presented on the surface of the cell as MHC-associated complexes, in a manner capable of being recognized by the immune system (e.g., MHC class I restricted cytotoxic T lymphocytes and/or MHC class II restricted helper T lymphocytes). The two requisite properties that allow a cell to function as an APC are the ability to process endocytosed antigens and the expression of MHC gene products. Examples of APCs include dendritic cells (DC), mononuclear phagocytes (e.g., macrophages), B lymphocytes, Langerhans cells of the skin and, in humans, endothelial cells.

The term “dendritic cell (DC)” as used herein, includes immature and mature DCs and related myeloid progenitor cells that are capable of differentiating into DCs or related antigen presenting cells (e.g., monocytes and macrophages). DCs express high levels of cell surface molecules and complementary receptors that interact with T lymphocytes (e.g., C-type lectins, such as the mannose receptor) and, therefore, are capable of inducing induce potent immune responses. DCs also secrete cytokines, chemokines and proteases which initiate an immune response and culminates in the amplification of both cellular and humoral immunity. DCs also express on their surface major histocompatibilty complex (MHC) molecules that bind fragments of antigens. T cells which recognize these antigen-MHC complexes become activated and initiate the immune cascade. In a preferred embodiment, binding of an antibody portion of the molecular conjugate of the invention to a dendritic cell results in internalization of the conjugate by the dendritic cell.

The term "macrophage mannose receptor" or "MR" refers to a member of a family of C-type lectin receptors characterized by repeated carbohydrate-recognition domains (CRD) in the extracellular portion and a short cytoplasmic tail containing two putative clathrin targeting sequences (34, 35, 37). In addition, the MR contains N-terminal cysteine rich and fibronectin domains. The different domains of the mannose receptor have specific binding capacity for various ligands including lysosomal enzymes, micro-organisms, pituitary hormones, glycosoaminoglycans, and sulfated blood group antigens (38-40).

"MHC molecules" include two types of molecules, MHC class I and MHC class II. MHC class I molecules present antigen to specific CD8$^{30}$ T cells and MHC class II molecules present antigen to specific CD4$^+$ T cells. Antigens delivered exogenously to APCs are processed primarily for association with MHC class II. In contrast, antigens delivered endogenously to APCs are processed primarily for association with MHC class I. However, under specific conditions, DCs have the unique capacity to allow exogenous antigens access to internal compartments for binding to MHC class I molecules, in addition to MHC class II molecules. This process is called "cross-priming" or "cross-presentation."

As used herein, the term "immunostimulatory agent" refers to compounds capable of stimulating APCs, such as DCs and macrophages. For example, suitable immunostimulatory agents for use in the present invention are capable of stimulating APCs so that the maturation process of the APCs is accelerated, the proliferation of APCs is increased, and/or the recruitment or release of co-stimulatory molecules (e.g., CD80, CD86, ICAM-1, MHC molecules and CCR7) and pro-inflammatory cytokines (e.g., IL-1β, IL-6, IL-12, IL-15, and IFN-γ) is upregulated. Suitable immunostimulatory agents are also capable of increasing T cell proliferation. Such immunostimulatory agents include, but are not be limited to, CD40 ligand; cytokines, such as IFN-α, IFN-β, IFN-γ and IL-2; colony-stimulating factors, such as G-CSF (granulocyte colony-stimulating factor) and GM-CSF (granulocyte-macrophage colony-stimulating factor); an anti-CTLA-4 antibody; toll receptor agonists (e.g., flagellin and MALP-2 (macrophage activating lipopeptide-2); LPS (endotoxin); R837 (3M Pharmaceuticals, St. Paul, Minn.); R848 (3M Pharmaceuticals, St. Paul, Minn.); polyI:C (inosine:cytosine polynucleotide); ssRNA; dsRNA; Bacille Calmette-Guerin (BCG); Levamisole hydrochloride; and intravenous immune globulins.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, the term antigen "cross-presentation" refers to presentation of exogenous protein antigens to T cells via MHC class I and class II molecules on APCs.

As used herein, the term "T cell-mediated response" refers to any response mediated by T cells, including effector T cells (e.g., CD8$^+$ cells) and helper T cells (e.g., CD4$^+$ cells). T cell mediated responses include, for example, T cell cytotoxicity and proliferation.

As used herein, the term "cytotoxic T lymphocyte (CTL) response" refers to an immune response induced by cytotoxic T cells. CTL responses are mediated primarily by CD8$^+$ T cells.

As used herein, the term "antibody" includes whole antibodies or antigen-binding fragments thereof including, for example, Fab, F(ab')$_2$, Fv and single chain Fv fragments. Suitable antibodies include any form of antibody, e.g., murine, human, chimeric, or humanized and any type antibody isotype, such as IgG1, IgG2, IgG3, IgG4, IgM, IgA1, IgA2, IgAsec, IgD, or IgE isotypes. As used herein, "isotype" refers to the antibody class that is encoded by heavy chain constant region genes.

Whole antibodies contain at least two heavy (H) chains and two light (L) chains inter-connected by disulfide bonds. Each heavy chain is comprised of a heavy chain variable region (abbreviated herein as HCVR or $V_H$) and a heavy chain constant region. The heavy chain constant region is comprised of three domains, CH1, CH2 and CH3. Each light chain is comprised of a light chain variable region (abbreviated herein as LCVR or $V_L$) and a light chain constant region. The light chain constant region is comprised of one domain, CL. The $V_H$ and $V_L$ regions can be further subdivided into regions of hypervariability, termed "complementarity determining regions (CDR)", interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

Preferred antibodies of the invention include human antibodies, e.g., a human antibody having an IgG1 (e.g., IgG1k) heavy chain and a kappa light chain. Other preferred antibodies of the invention bind human DCs, such as antibodies which bind a C-type lectin receptor on a human DC, e.g., the MR on human DCs. In a particular embodiment, the antibody is a human monoclonal antibody that binds to the human macrophage mannose receptor (also referred to herein as "human B11 antigen") having an approximate molecular weight of 180 kD as measured by SDS-PAGE. Protocols for generating such antibodies are described in WO 01/085798, the contents of which are incorporated herein by reference. Particular human antibodies include those which comprise heavy and light chain variable regions amino acid sequences as shown in SEQ ID NOs: 2 and 6, respectively, or an amino acid sequence that is sufficiently homologous to SEQ ID NO:2 or SEQ ID NO:6 such that the antibody retains the ability to bind to dendritic cells.

The term "antigen-binding portion" of an antibody (or simply "antibody portion"), as used herein, refers to one or more fragments of an antibody that retain the ability to specifically bind to an antigen (e.g., an antigen on a dendritic cell). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The term "human antibody," as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The terms "monoclonal antibody" or "monoclonal antibody composition," as used herein, refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene, fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "specific binding" refers to antibody binding to a predetermined antigen. Typically, the antibody binds with a dissociation constant ($K_D$) of $10^{-7}$ M or less, and binds to the predetermined antigen with a $K_D$ that is at least two-fold less than its $K_D$ for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

As used herein, the term "high affinity" for an IgG antibody refers to an antibody having a $K_D$ of $10^{-8}$ M or less, more preferably $10^{-9}$ M or less and even more preferably $10^{-10}$ M or less. However, "high affinity" binding can vary for other antibody isotypes. For example, "high affinity" binding for an IgM isotype refers to an antibody having a $K_D$ of $10^{-7}$ M or less, more preferably $10^{-8}$ M or less.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M).

As used herein, the term "βhCG" refers to the beta subunit of human chorionic gonadotropin and includes the whole antigen, antigenic fragments thereof, allelic variants thereof, and any polymorphisms, derived from the βhCG sequence (SEQ ID NO:20). βhCG is a hormone necessary for the establishment of a successful pregnancy. Aside from pregnancy, the expression of this antigen is primarily restricted to germ cell tumors, as well as a significant number of adenocarcinomas.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule," is used herein in reference to nucleic acids encoding the molecular conjugates of the invention or portions thereof, e.g., SEQ ID NOs:9 and 11 or portions thereof, such as the antigen or antibody portions (i.e., the $V_H$, $V_L$, or CDRs). Isolated nucleic acid molecules refer to a nucleic acid molecule in which the nucleotide sequences encoding the molecular conjugates are free of other contaminating nucleotide sequences, e.g., a nucleotide sequence which does not encode any part of the molecular conjugate.

As disclosed and claimed herein, the sequences set forth in SEQ ID NOs: 1-28 can include "conservative sequence modifications," i.e., nucleotide and amino acid sequence modifications which do not significantly affect or alter the functional characteristics of the molecular conjugate, e.g., the binding properties of the antibody portion of the construct or the immunogenic properties of the antigen portion, encoded by the nucleotide sequence or containing the amino acid sequence. Such conservative sequence modifications include nucleotide and amino acid substitutions, additions and deletions. Modifications can be introduced into SEQ ID NOs: 1-28 by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-DCs antibody is preferably replaced with another amino acid residue from the same side chain family.

Alternatively, in another embodiment, mutations can be introduced randomly along all or part of a molecular conjugate coding sequence, such as by saturation mutagenesis, and the resulting modified molecular conjugates can be screened for appropriate functional activity.

Accordingly, molecular conjugates encoded by the nucleotide sequences disclosed herein and/or containing the amino acid sequences disclosed herein (i.e., SEQ ID NOs: 1-28) include substantially similar conjugates encoded by or containing similar sequences which have been conservatively modified. In particular, discussion as to how substantially similar antibodies can be generated for use in the molecular conjugates based on the partial (i.e., heavy and light chain variable regions) sequences (SEQ ID NOs: 3, 4, 7, and 8) is provided below.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at the GCG website), using a NWSgapdna.CMP matrix and a gap weight of 40, 50, 60, 70, or 80 and a length weight of 1, 2, 3, 4, 5, or 6. The percent identity between two nucleotide or amino acid sequences can also determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at the GCG website), using either a Blossum 62 matrix or a PAM250 matrix, and a gap weight of 16, 14, 12, 10, 8, 6, or 4 and a length weight of 1, 2, 3, 4, 5, or 6

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (19906) *J. Mol. Biol.* 215:403-10. BLAST nucleotide searches can be performed with the NBLAST program, score =100, wordlength =12 to obtain nucleotide sequences homologous to the nucleic acid molecules of the invention. BLAST protein searches can be performed with the)(BLAST program, score =50, wordlength =3 to obtain amino acid sequences homologous to the protein molecules of the invention. To obtain gapped alignments for comparison purposes, Gapped BLAST can be utilized as described in Altschul et al., (1997) *Nucleic Acids Res*. 25(17):3389-3402. When utilizing BLAST and Gapped BLAST programs, the default parameters of the respective programs (e.g., XBLAST and NBLAST) can be used. See the NCBI website.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. *Current Protocols in Molecular Biology*, Greene Publishing and Wiley Interscience, New York (1987).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, CHO cells and lymphocytic cells.

As used herein, the term "subject" includes any human or nonhuman animal. The term "nonhuman animal" includes all vertebrates, e.g., mammals and non-mammals, such as non-human primates, sheep, dog, cow, chickens, amphibians, reptiles, etc.

Various aspects of the invention are described in further detail in the following subsections.

I. Antigens

Suitable antigens for use in the present invention include, for example, infectious disease antigens and tumor antigens, against which protective or therapeutic immune responses are desired, e.g., antigens expressed by a tumor cell or a pathogenic organism or infectious disease antigens. For example, suitable antigens include tumor-associated antigens for the prevention or treatment of cancers. Examples of tumor-associated antigens include, but are not limited to, βhCG, gp100 or Pmel17, HER2/neu, CEA, gp100, MARTI, TRP-2, melan-A, NY-ESO-1, MN (gp250), idiotype, MAGE-1, MAGE-3, Tyrosinase, Telomerase, MUC-1 antigens, and germ cell derived tumor antigens. Tumor associated antigens also include the blood group antigens, for example, $Le^a$, $Le^b$, LeX, LeY, H-2, B-1, B-2 antigens. Alternatively, more than one antigen can be included within the antigen-antibody constructs of the invention. For example, a MAGE antigen can be combined with other antigens such as melanin A, tyrosinase, and gp100 along with adjuvants such as GM-CSF or IL-12, and linked to an anti-APC antibody.

Other suitable antigens include viral antigens for the prevention or treatment of viral diseases. Examples of viral antigens include, but are not limited to, HIV-1 gag, HIV-1 env, HIV-1 nef, HBV core, FAS, HSV-1, HSV-2, p17, ORF2 and ORF3 antigens. Examples of bacterial antigens include, but are not limited to, *Toxoplasma gondii* or *Treponema pallidum*. The antibody-bacterial antigen conjugates of the invention can be in the treatment or prevention of various bacterial diseases such as Anthrax, Botulism, Tetanus, *Chlamydia*, Cholera, Diptheria, Lyme Disease, Syphilis and Tuberculosis.

In a particular embodiment exemplified herein, the present invention employs an antigen comprising βhCG. This includes the entire βhCG sequence (SEQ ID NO:20) or any immunogenic (e.g., T cell epitope containing) portion of the sequence. As described below, such immunogenic portions can be identified using techniques known in the art for mapping T cell epitopes, including algorithms and known T cell epitope mapping techniques. Examples of particular immunogenic peptides from βhCG include those comprising SEQ ID NOs:21, 22, 23, 24, 25, 26, 27, or 28, and conservative modifications thereof. Additional immunogenic peptides from βhCG, and methods for identifying such peptides, are described in U.S. Pat. Nos. 6,096,318 and 6,146,633, the contents of which are incorporated by reference herein.

Figure 10:
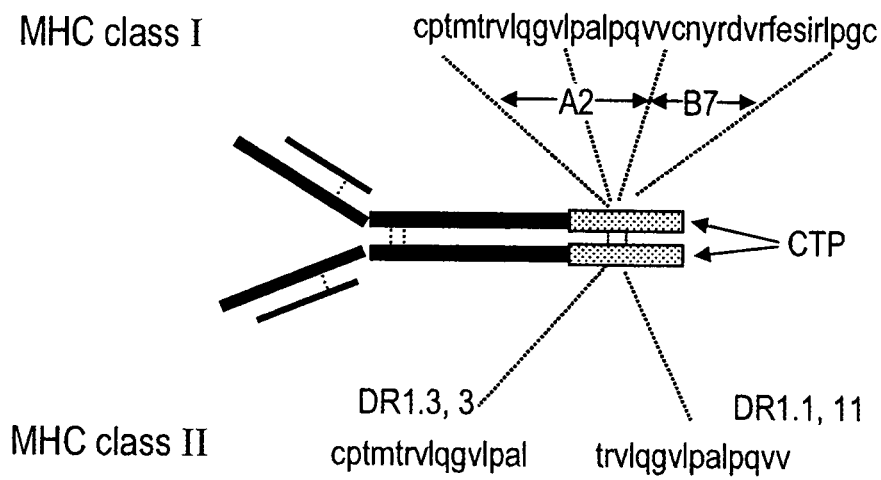
FIG. 10 is a diagram showing the predicted T cell epitopes of the βhCG-B11 construct as analyzed using web-based predictive algorithms (BIMAS & SYFPEITHI). T cell epitopes were found for potential binding to HLA-A2, HLA-B7 and HLA-DR molecules. Several epitopes were also predicted from the B11 segment of βhCG-B11. No T cell epitope was identified in the 37 aa long C-terminal peptide.

Antigenic peptides of proteins (i.e., those containing T cell epitopes) can be identified in a variety of manners well known in the art. For example, T cell epitopes can be predicted by analyzing the sequence of the protein using web-based predictive algorithms (BIMAS & SYFPEITHI) to generate potential MHC class I and II-binding peptides that match an internal database of 10,000 well characterized MHC binding peptides previously defined by CTLs. High scoring peptides can be ranked and selected as "interesting" on the basis of high affinity to a given MHC molecule. As shown in FIG. 10 and using the sequence of the βhCG-B11 conjugate (SEQ ID NO: 10), both algorithms were used to identify antigenic peptides from the βhCG portion (mustard) from which synthetic versions could be made and tested for their capacity to elicit T cell responses in vitro. Thus, T cell epitopes were found for potential binding to HLA-A2, HLA-B7 and HLA-DR molecules. Several epitopes were also predicted from the antibody (B11) segment of the βhCG-B11 conjugate (results not shown). Further, no T cell epitope was identified in the 37 amino acid long C-terminal peptide (CTP).

Another method for identifying antigenic peptides containing T cell epitopes is by dividing the protein into non-overlapping peptides of desired length or overlapping peptides of desired lengths which can be produced recombinantly, synthetically, or in certain limited situations, by chemical cleavage of the protein and tested for immunogenic properties, e.g., eliciting a T cell response (i.e., proliferation or lymphokine secretion).

In order to determine precise T cell epitopes of the protein by, for example, fine mapping techniques, a peptide having T cell stimulating activity and thus comprising at least one T cell epitope, as determined by T cell biology techniques, can be modified by addition or deletion of amino acid residues at either the amino or carboxy terminus of the peptide and tested to determine a change in T cell reactivity to the modified peptide. If two or more peptides which share an area of overlap in the native protein sequence are found to have human T cell stimulating activity, as determined by T cell biology techniques, additional peptides can be produced comprising all or a portion of such peptides and these additional peptides can be tested by a similar procedure. Following this technique, peptides are selected and produced recombinantly or synthetically. Peptides are selected based on various factors, including the strength of the T cell response to the peptide (e.g., stimulation index). The physical and chemical properties of these selected peptides (e.g., solubility, stability) can then be examined to determine whether the peptides are suitable for use in therapeutic compositions or whether the peptides require modification.

II. Antibody Vaccine Conjugates

The present invention provides a variety of therapeutic vaccine conjugates which include an antigen, such as a tumor or viral antigen, linked to an antibody that binds to an APC, e.g., via the mannose receptor (MR). This allows for targeting of the antigen to APCs (e.g., dendritic cells) to enhance processing, presentation and, ultimately, an immune response against the antigen(s), e.g., a CTL response.

In addition, the vaccine conjugate can include one or more immunostimulatory agents that also enhance the immune response against the antigen. Antibody-antigen vaccine conjugates of the invention can be made genetically or chemically. In either case, the antibody portion of the conjugate may consist of the whole antibody or a portion of the antibody, such as the Fab fragment or single-chain Fv. In addition, more than one antigen and/or immunostimulatory agent can be included in the conjugate.

In one embodiment, the vaccine conjugate comprises a human antibody heavy chain that binds to human APCs and a human antibody light chain that binds to human APCs, wherein either or both chains are linked to the antigen and to an immunostimulatory agent. In another embodiment, the antigen and the immunostimulatory agent are separately linked to either chain. In a particular embodiment, the antigen is βhCG.

Genetically constructed anti-dendritic antibody-antigen conjugates (e.g., those expressed as a single recombinant fusion protein) can be made by linking an antigen of choice and/or an immunostimulatory agent (in the case of protein and peptide immunostimulatory agents) to the antibody at a variety of locations. Particular genetically produced conjugates (fusion constructs) of the invention include, for example, the βhCG-B11 construct, shown in FIG. 2. The βhCG-B11 construct comprises human anti-dendritic cell antibody B11 fused to βhCG, a tumor-associated antigen. The nucleotide sequence encoding this construct is shown in SEQ ID NO:9.

For example, in one embodiment, the βhCG antigen and/or the immunostimulatory agent can be fused to the end of the $CH_3$ domain of the human antibody heavy chain. The antigen and/or immunostimulatory agent also can be fused at the hinged region of the antibody heavy chain in Fab-fusion constructs, or in sequence with the variable light and heavy chains ($V_H$ and $V_L$) in single chain fusion constructs (ScFv constructs). Alternatively, the antigen and/or immunostimulatory agent can be fused to the antibody light chain instead of the antibody heavy chain. Other points of fusion among the immunostimulatory agent, the antigen and the antibody can be used provided the genetic fusion construct can elicit a CTL response. A detailed map of the intact βhCG-B11 construct and the single chain B11 construct (pB11 sfv-βhCG) are shown in Tables 1 and 2, respectively. Such genetic fusion conjugates can include an antigen and an immunostimulatory agent linked to the antibody in either order (e.g., an antibody-antigen-immunostimulatory conjugate or an antibody-immunostimulatory agent-antigen conjugate).

TABLE 1

βhCG-B11 Feature Map

CDS (3 total)
    BUsfr-bHCG
        Start: 921 End: 2153 neo
        Start 3375 End: 4169 neomycin resistance gene
    Amp
        Start: 5671 End: 6531 (Complementary) Ampicillin resistance gene
Misc. Feature (5 total)
    promoter
        Start: 863 End: 882 promoter
    signal sequence
        Start 921 End: 977 B11 VL
        Start: 978 End: 1296 B11 VH
        Start: 1344 End: 1691 beta HCG
        Start: 1712 End: 2164
PolyA Signal (2 total)
    poly A
        Start: 2267 End: 2491 poly A
    poly A
        Start: 4343 End: 4473 SV40 poly A signal
Promoter Eukaryotic (1 total)
    promoter
        Start: 232 End: 819 eukaryotic promoter
Promoter Prokaryotic (1 total)
    promoter
        Start 6566 End: 6572 (Complementary) promoter
Replication Origin (3 total)
    SV40 promoter and origin
        Start 1 End: 1 origin of replication
    F1 origin
        Start: 2537 End: 2965 origin of replication
    pUC origin
    Start 4856 End: 5526 (Complementary) origin

TABLE 2 pB11sfv-βhCG Feature Map

CDS (4 total)
    Light Chain
        Start 735 End: 1433 B11 Light Chain
    C kappa
        Start: 1113 End: 1433 AMP
        Start: 7810 End: 8670 (Complementary) amp
        Original Location Description: complemented 1 . . . 6871)
    DHFR
        Start: 8921 End: 9484 dhfr
        Original Location Description: 7122–7685

TABLE 2-continued pB11sfv-βhCG Feature Map

Misc. Feature (9 total)
    B11 VL
        Start: 792 End: 1112 SV40 Promoter/Ori
        Start 2298 End: 2622
        SV40 promoter and origan of replication
    Neo
        Start: 2658 End: 3452 Neomicin Resistance Gene
    beta HCG
        Start: 4015 End: 4467 (Complementary) bHCG
    CHS
        Start: 4470 End: 4790 (Complementary) Heavy chain constant region 3
    CH2
        Start: 4791 End: 5120 (Complementary) Heavy chain constant region 2
    CH1
        Start 5166 End: 5459 (Complementary) heavy chain constant region 1
    B11 VH
        Start: 5460 End: 5807 (Complementary) Promoter
        Start: 5905 End: 6559 (Complementary)
PolyA Signal (3 total)
    Poly A
        Start: 1526 End: 1757 PolyA
        Start: 3744 End: 3975 (Complementary) PolyA_Signal_2
        Start 10282 End: 10411 SV40 poly A
        Original Location Description: 8483 . . . 8612
Promoter Eukaryotic (1 total)
    Promoter
        Start 9 End: 655

Chemically constructed antibody-antigen conjugates can be made using a variety of well known and readily available cross-linking reagents. These cross-linking reagents can be homofunctional or heterofunctional compounds, such as N-succinimidyl-3-(2-pyridyldithio)propionate (SPDP), N-succinimidyl-S-acetyl-thioacetate (SATA), sulfosuccinimidyl 4-(N-maleimidomethyl) cyclohaxane-1-carboxylate (sulfo-SMCC), 5,5'-dithiobis(2-nitrobenzoic acid) (DTNB), that form covalent linkages with different reactive amino acid or carbohydrate side chains on the anti-dendritic antibody and selected antigen. Other coupling and cross-linking agents also can be used to generate covalent linkages, such as protein A, carbodiimide, and o-phenylenedimaleimide (oPDM); (see e.g., Karpovsky et al. (1984) J. Exp. Med. 160:1686; Liu, M A et al. (1985) Proc. Natl. Acad. Sci. USA 82:8648). Other methods include those described by Paulus (Behring Ins. Mitt. (1985) No. 78, 118-132); Brennan et al. (Science (1985) 229:81-83), and Glennie et al. (J. Immunol. (1987) 139: 2367-2375). Preferred conjugating agents are SATA and sulfo-SMCC, both available from Pierce Chemical Co. (Rockford, Ill.). Immunostimulatory agents can also be chemically linked to the molecular conjugates of the present invention using the same linking methods described above.

Immunostimulatory agents and molecular conjugates can also be linked via non-covalent methods, for example, using binding molecules such as streptavidin and biotin. Other suitable binding molecules for use in the present invention are well-known in the art. In one aspect of the invention, the nucleotide sequence encoding a streptavidin molecule is incorporated into the sequence encoding the molecular conjugate which, in turn, is linked to a biotinylated immunostimulatory agent.

Any antigen that can be cloned and expressed or purified can be selected for use in the present invention. Techniques for obtaining such antigens are well-known in the art. For example, tumor-associated antigens can be directly purified from cancer cells and identified by physiochemical techniques such as tandem mass spectrometry. Alternatively, tumor-specific T-cell clones can be tested against antigen-negative cells that have acquired antigen by being transfected with plasmid DNA clones to isolate the clone expressing the antigen. Synthetic peptides can then be constructed to precisely identify the antigenic site or epitope.

As discussed above, the molecular vaccine conjugates of the invention can be administered together with, or include, one or more immunostimulatory agents. The immunostimulatory agent can be administered separately or can be linked to the conjugate, either covalently, non-covalently, genetically, or a combination thereof, according to the linking techniques discussed above. Alternatively, the immunostimulatory agent can be co-administered separately, for example, the agent can be administered simultaneously with the molecular conjugate, or prior to administration of the molecular conjugate, or subsequent to administration of the molecular conjugate. A variety of suitable immunostimulatory agents are well known in the art and include, for example, CD40 ligand; cytokines, such as IFN-α, IFN-β, IFN-γ and IL-2; colony-stimulating factors, such as G-CSF (granulocyte colony-stimulating factor) and GM-CSF (granulocyte-macrophage colony-stimulating factor); an anti-CTLA-4 antibody; toll receptor agonists (e.g., flagellin and MALP-2 (macrophage activating lipopeptide-2); LPS (endotoxin); R837 (3M Pharmaceuticals, St. Paul, Minn.); R848 (3M Pharmaceuticals, St. Paul, Minn.); polyI:C (inosine:cytosine polynucleotide); ssRNA; dsRNA; Bacille Calmette-Guerin (BCG); Levamisole hydrochloride; and intravenous immune globulins.

In another aspect of the invention, partial antibody sequences from the vaccine construct can be used to express intact antibodies. Antibodies, such as the anti-APC antibodies (e.g., B11) encompassed by the vaccine conjugates of the present invention, interact with target antigens (e.g., C-type lectin receptors, such as the MR) predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332:323-327; Jones, P. et al. (1986) Nature 321:522-525; and Queen, C. et al. (1989) Proc. Natl. Acad. See. U.S.A. 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region. For example, somatic mutations are relatively infrequent in the amino-terminal portion of framework region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see WO 99/45962, which is herein incorporated by referenced for all purposes). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. For this reason, it is necessary to use the corresponding germline leader sequence for expression constructs. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from hybridomas are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak (1991) J. Biol. Chem. 266:19867-19870); and HindIII sites are engineered upstream of the translation initiation sites.

For both the heavy and light chain variable regions, the optimized coding, and corresponding non-coding, strand sequences are broken down into 30-50 nucleotide approximately the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region (including the BbsI site of the kappa light chain, or the AgeI site of the gamma heavy chain) in the PCR amplification to generate fragments that can easily be cloned into the expression vector constructs.

The reconstructed heavy and light chain variable regions are then combined with cloned promoter, translation initiation, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Plasmids for use in construction of expression vectors for human IgGκ are described below. The plasmids were constructed so that PCR amplified V heavy and V kappa light chain cDNA sequences could be used to reconstruct complete heavy and light chain minigenes. These plasmids can be used to express completely human, or chimeric $IgG_1κ$ or $IgG_4κ$ antibodies. Similar plasmids can be constructed for expression of other heavy chain isotypes, or for expression of antibodies comprising lambda light chains.

Thus, in another aspect of the invention, the structural features of the antibody portion of the vaccine conjugates described herein, e.g., B11, are used to create structurally related antibodies that retain at least one functional property of the B11 antibody of the invention, such as binding to APCs. More specifically, one or more CDR regions of B11 can be combined recombinantly with known human framework regions and CDRs to create additional, recombinantly-engineered, anti-APC antibodies for use in the vaccine conjugates of the invention.

Accordingly, in another embodiment, the invention provides a method for preparing a vaccine conjugate comprising an anti-DC antibody comprising: preparing an antibody comprising (1) human heavy chain framework regions and human heavy chain CDRs, wherein at least one of the human heavy chain CDRs comprises an amino acid sequence selected from the amino acid sequences of CDRs shown in FIG. 8 (SEQ ID NOs:13, 14, or 15); and (2) human light chain framework regions and human light chain CDRs, wherein at least one of the human light chain CDRs comprises an amino acid sequence selected from the amino acid sequences of CDRs shown in FIG. 9 (SEQ ID NO:16, 17, or 18); wherein the antibody retains the ability to bind to APCs.

The ability of the antibody to bind APCs can be determined using standard binding assays, such as those set forth in the Examples (e.g., an ELISA). Since it is well known in the art that antibody heavy and light chain CDR3 domains play a particularly important role in the binding specificity/affinity of an antibody for an antigen, the recombinant antibodies of the invention prepared as set forth above preferably comprise the heavy and light chain CDR3s of B11. The antibodies further can comprise the CDR2s of B11. The antibodies further can comprise the CDR1s of B11. Accordingly, the invention further provides anti-APC antibodies comprising: (1) human heavy chain framework regions, a human heavy chain CDR1 region, a human heavy chain CDR2 region, and a human heavy chain CDR3 region, wherein the human heavy chain CDR3 region is the CDR3 of B11 as shown in FIG. 8 (SEQ ID NO: 15); and (2) human light chain framework regions, a human light chain CDR1 region, a human light chain CDR2 region, and a human light chain CDR3 region, wherein the human light chain CDR3 region is the CDR3 of B11 as shown in FIG. 9 (SEQ ID NO: 18), wherein the antibody binds DC. The antibody may further comprise the heavy chain CDR2 and/or the light chain CDR2 of B11. The antibody may further comprise the heavy chain CDR1 and/or the light chain CDR1 of B11.

Preferably, the CDR1, 2, and/or 3 of the engineered antibodies described above comprise the exact amino acid sequence(s) as those of B11 disclosed herein. However, the ordinarily skilled artisan will appreciate that some deviation from the exact CDR sequences of B11 may be possible while still retaining the ability of the antibody to bind DC effectively (e.g., conservative substitutions). Accordingly, in another embodiment, the engineered antibody may be composed of one or more CDRs that are, for example, at least 90%, 95%, 98% or 99.5% identical to one or more CDRs of B11.

In addition or alternatively to simply binding APCs, engineered antibodies such as those described above may be selected for their retention of other functional properties of antibodies of the invention, such as:

(1) high affinity binding to APCs;
(2) binding to a unique epitope on an APC (to eliminate the possibility that monoclonal antibodies with complimentary activities when used in combination would compete for binding to the same epitope);
(3) induces a T cell-mediated immune response which is generated against the antigen; and/or (4) induces a T cell response which comprises both $CD4^+$ and $CD8^+$ T cell-mediated responses.

In another embodiment, a whole cell expressing the antigen of interest, e.g., βhCG, is transformed to express an anti-APC antibody, e.g., an anti-MR antibody, so that the antigen and the antibody are co-expressed by the cell. This can be done, for example, by transfecting the target cell with a nucleic acid encoding a fusion protein containing a transmembrane domain and an anti-APC antibody. The cell expressing the vaccine conjugate can then be used to target APCs, e.g., DCs, to induce a CTL response.

Methods for generating such nucleic acids, fusion proteins, and cells expressing such fusion proteins are described, for example, in U.S. patent application Ser. No. 09/203,958, incorporated herein in its entirety by this reference.

Alternatively, the antibody can be bound to a cell or a pathogen by the use of chemical linkers, lipid tags, or other related methods (deKruif, J. et al. (2000) *Nat. Med.* 6:223-227; Nizard, P. et al. (1998) FEBS Lett. 433:83-88). Cells which express the antigen of interest and with surface-anchored antibodies may be used to induce specific immune responses, e.g., a CTL response, against the cell, e.g., a tumor cell or microbial pathogen.

III. Pharmaceutical Compositions

In another aspect, the present invention provides therapeutic compositions, e.g., pharmaceutical compositions, containing one or a combination of vaccine conjugates of the present invention formulated together with an immunostimulatory agent. In one embodiment, the immunostimulatory agent is linked to the vaccine conjugate. The compositions of the present invention may further include one or more adjuvants and/or pharmaceutically acceptable carrier. The vaccine conjugate of the present invention is administered for delivery into the subject's bloodstream for interaction with the subject's T cells. Such targeting of T cells can be accomplished either in vivo or ex vivo by directly using the conjugate or by using cells which have been previously been targeted with vaccine conjugates.

The compositions of the present invention can additionally include other therapeutic reagents, such as other antibodies, cytotoxins or drugs (e.g., immunosuppressants), and can be administered alone or in combination with other therapies, such as radiation. For example, a vaccine conjugate that is rapidly internalized by APCs can be combined with a monoclonal antibody that enhances antigen presenting cell activities of dendritic cells, e.g., release of immunostimulatory cytokines.

As used herein, "pharmaceutically acceptable carrier" includes any and all solvents, dispersion media, coatings, antibacterial and antifingal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the vaccine conjugate may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Compositions of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

To administer a vaccine conjugate of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.01 to 99.5% (more preferably, 0.1 to 90%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic compositions may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

IV. Uses and Methods of the Invention

Vaccine conjugates of the present invention can be used to treat and/or prevent (e.g., immunize against) a variety of diseases and conditions.

One of the primary disease indications is cancer. This includes, but is not limited to, colon cancer, melanoma, lymphoma, prostate carcinoma, pancreatic carcinoma, bladder carcinoma, fibrosarcoma, rhabdomyosarcoma, mastocytoma, mammary adenocarcinoma, leukemia, or rheumatoid fibroblastsoma. Another primary disease indication is infectious diseases including, but not limited to, HIV, Hepatitis (e.g., A, B, & C), Influenza, Herpes, *Giardia*, Malaria, *Leishmania, Staphylococcus Aureus, Pseudomonas aeruginosa*. Another primary disease indication is autoimmune diseases.

In a particular embodiment, the vaccine conjugates are used to treat or prevent diseases and conditions mediated by βhCG or cells expressing βhCG, which is a member of the cysteine-loop growth factor superfamily. Evidence suggests that βhCG plays a role in the establishment or progression of cancers either as a growth factor, as an angiogenesis and/or metastasis-promoting agent, or as a suppressor of immune function (73). Accordingly, the present invention can be used to treat the progression of cancers and other diseases involving angiogenesis. The invention also can be used to prevent or terminate unwanted pregnancy by inhibiting the role of βhCG and/or cells expressing βhCG in pregnancy.

For use in therapy, vaccine conjugates of the invention can be administered to a subject directly (i.e., in vivo), either alone or with an immunostimulatory agent. In one aspect, the immunostimulatory agent is linked to the conjugate. Alternatively, the conjugates can be administered to a subject indirectly by first contacting the conjugates (e.g., by culturing or incubating) with APCs, such as dendritic cells, and then administering the cells to the subject (i.e., ex vivo). The contacting and delivering of the conjugates to APCs, such that they are processed and presented by the APCs prior to administration, is also referred to as antigen or cell "loading." Techniques for loading antigens to APCs are well known in the art and include, for example, Gunzer and Grabbe, Crit Rev Immunol 21 (1-3):133-45 (2001) and Steinman, Exp Hematol 24(8): 859-62 (1996).

In all cases, the vaccine conjugates and the immunostimulatory agents are administered in an effective amount to exert their desired therapeutic effect. The term "effective amount" refers to that amount necessary or sufficient to realize a desired biologic effect. For example, an effective amount could be that amount necessary to eliminate a tumor, cancer, or bacterial, viral or fungal infection. The effective amount for any particular application can vary depending on such factors as the disease or condition being treated, the particular conjugate being administered, the size of the subject, or the severity of the disease or condition. One of ordinary skill in the art can empirically determine the effective amount of a particular multi specific molecule without necessitating undue experimentation.

Preferred routes of administration for the vaccine conjugates include, for example, injection (e.g., subcutaneous, intravenous, parenteral, intraperitoneal, intrathecal). The injection can be in a bolus or a continuous infusion. Other routes of administration include oral administration.

Vaccine conjugates of the invention also can be coadministered with adjuvants and other therapeutic agents, such as immunostimulatory agents. The conjugates are typically formulated in a pharmaceutically acceptable carrier alone or in combination with such agents. Examples of such carriers include solutions, solvents, dispersion media, delay agents, emulsions and the like. The use of such media for pharmaceutically active substances are well known in the art. Any other conventional carrier suitable for use with the molecules falls within the scope of the instant invention.

Suitable agents for coadministration with the vaccine conjugates include other antibodies, cytotoxins and/or drugs. In one embodiment, the agent is a anti-CTLA-4 antibody which are known to aid or induce immune responses. In another embodiment, the agent is a chemotherapeutic agent. The vaccine conjugates also can be administered in combination with radiation.

The present invention is further illustrated by the following examples which should not be construed as further limiting. The contents of all figures and all references, patents and published patent applications cited throughout this application are expressly incorporated herein by reference.

EXAMPLES

Methods and Materials

Generation of DCs from whole blood or leukopak: Human peripheral blood mononuclear cells (PBMC) were obtained by density gradient centrifugation of heparinized whole blood or apheresis preparations with Ficoll-Paque. Monocytes were then isolated by adherence to plastic culture dishes or elutriation and differentiated into immature DCs by addition of cytokines (10 ng/ml GM-CSF and 2 ng/ml IL-4) to the culture medium. DCs were harvested between day 5 and 7 and analyzed by flow cytometry. The DCs prepared in this fashion were $CD14^-$, $HLA-DR^+$, $CD11c^+$ mannose receptor$^+$ and expressed high levels of MHC Class I and II, CD80 and CD86.

Selection of tumor antigen βhCG: βhCG is a subunit of human chorionic gonadotropin, a hormone necessary for the establishment of a successful pregnancy. This glycoprotein subunit has a number of features that make it an attractive antigen for cancer immunotherapy (reviewed in Triozzi P. L. and Stevens V. (1999) Oncology Reports 6:7-17). First, aside from pregnancy, the expression of this antigen is primarily restricted to germ cell tumors, as well as a significant number of adenocarcinomas (Table 3). Also, hCG is a member of the cysteine-loop growth factor superfamily and may play a role in the a establishment or progression of cancers either as a growth factor, an angiogenesis and/or metastasis-promoting agent, or as a suppressor of immune function. Immunotherapy that limits the expression of functional hCG may therefore offer added therapeutic benefit.

TABLE 3

Percent of tumors positive for βhCG by immunohistochemistry (Triozzi P. L. and Stevens V. (1999)).

| |
| --- |
| Colon (52%) |
| Lung (34%) |
| Pancreas (31%) |
| Esophagus (28%) |
| Breast (24%) |
| Bladder (21%) |
| Ovary (19%) |
| Cervix (18%) |
| Gastric (18%) |

Proliferation Assay: Effector T cells ($5 \times 10^4$) were co-cultured with autologous DCs ($5 \times 10^3$) loaded with or without antigen (MDX-1307 or other) in 96 well flat bottomed microplates in 0.2 ml final volume. The mixture was cocultured at 37° C. On day 4, cultures were pulsed with $^3$H-thymidine (1 μCi/well) and 18 hours later, cells were harvested directly on filters (Millipore). Filters were washed three times with water followed by one wash in ethanol and allowed to dry under the hood for 5-10 min. Scintillation fluid (Packard, 20 μl/well) was then added to the filters. Filter-bound radioactivity was determined by counting on the Wallac beta counter. The results are expressed as stimulation index (S.I.) values in cpm of CTL stimulated with antigen versus stimulation with no antigen or control antigen. For MHC blocking analysis, labeled targets were preincubated with HLA-specific mAbs, W6/32 for blocking all class I and L243 for blocking all class II HLA molecules (20 μg/ml), for 30 min. at RT. Unbound mAb was removed by centrifugation.

Flow cytometry: Human DCs were prepared from monocytes by culture in GM-CSF and IL-4 for 5 days. DCs were incubated on ice with 10 μg/ml of the βhCG antigen/anti-MR antibody vaccine conjugate or an isotype control. Vaccine conjugates were either directly FITC-labeled or detected with an FITC-labeled anti-βhCG secondary monoclonal antibody. The cell associated fluorescence was determined using an LSR flow cytometer.

Cytotoxicity Assay: Target cells ($3 \times 10^6$), control and antigen loaded (βhCG-B11), were washed twice in RPMI medium and the pellet was resuspended in 200 μl medium and labeled with 100 μCi $^{51}Na_2CrO_4$ for 60 min at 37° C. Labeled targets were washed 3 times in RPMI medium and the pellet resuspended to yield a cell concentration of $3 \times 10^4$ cells/ml. Antigen-specific CTL were titrated in a 96 well V-bottomed plate to give ratios of 100:1 (effector T cell, E: target, T) through to 12.5:1 or lower. A constant number of labeled targets were added (100 µl/well or 3,000 target cells/well) and the plates were spun down at low speed (180×g) and incubated at 37° C. After 4 hours, 100-120 µl supernatant was harvested and the radioactivity released was determined in a γ-counter counting (Wallac Instruments, Perkin-Elmer). CTL activity was calculated and expressed as % Specific Lysis (killing) using the following equation:

Specific Lysis (%) =

$$\frac{\text{Experimental Release }(cpm) - \text{Spontaneous Release }(cpm)}{\text{Maximal Release }(cpm) - \text{Spontaneous Release }(cpm)} \times 100;$$

where Experimental (cpm) refers to radioactivity (chromium released) from wells containing CTL (E) and target (T); Spontaneous (cpm) refers to the radioactivity from wells with targets in 0.1 ml medium alone (i.e. no CTL added) while Maximal release refers to radioactivity from wells with targets in the presence of 0.1 ml detergent solution (Igepal CA 630; syn. NP-40; 5% solution in RPMI medium). Under well-controlled experimental conditions, Spontaneous release values should be 10% of Maximal release or less. For MHC blocking analysis, labeled targets were preincubated with HLA-specific mAbs, W6/32 for blocking all class I and L243 for blocking all class II HLA molecules (20 µg/ml) for 30 min. at RT. Unbound mAb was removed by centrifugation and mAb-coated targets were added to CTL. An isotype-matched mAb was used as a control.

Yet another way to look at cell-mediated immune responses is to investigate the proliferative capacity of antigen-driven T cells. Antigen-sensitized T cells tend to proliferate preferentially when previously exposed antigens are presented in the context of MHC class II and to a lesser extent, class I molecules. Thus, the enumeration of dividing cells by uptake of a radioactive tracer provides a measure of stimulation.

Example 1

Production of βhCG-B11

Figure 3:
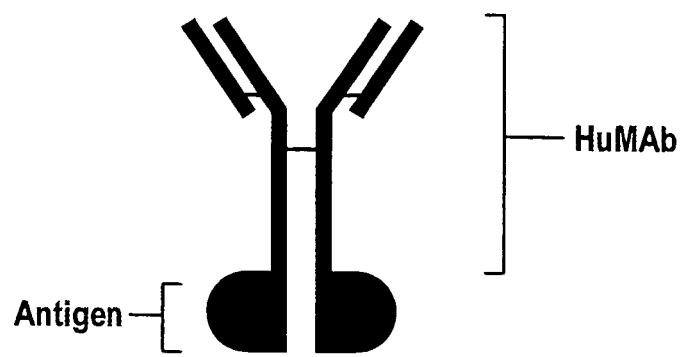
FIG. 3 is a schematic illustration of a molecular conjugate. The antigen is genetically fused to the heavy chains of the intact antibody.

Design of vaccine conjugate: This construct was generated by linking the βhCG antigen to B11, a fully human antibody which binds to the human macrophage mannose receptor on dendritic cells. Linkage was accomplished by covalently attaching the antigen to the heavy chain of the antibody by way of a genetic fusion, as shown in FIG. 3.

Figure 2:
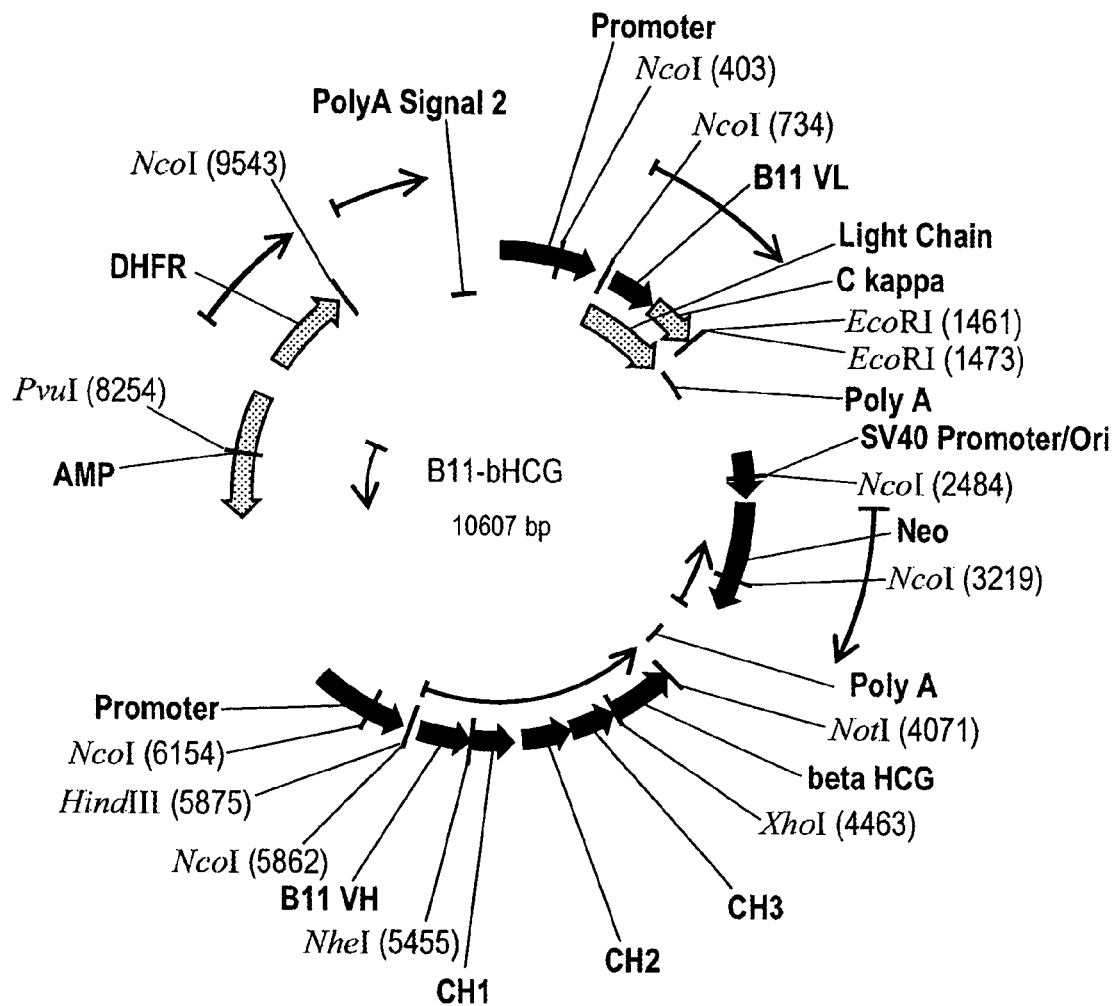
FIG. 2 shows a map of the molecular conjugate (SEQ ID NOs:9 and 10) encoding a fusion protein containing the whole B11 antibody linked to βhCG antigen (βhCG-B11 construct).

Recombinant Expression of βhCG-B11 Vaccine Conjugate: As shown in FIG. 2, a plasmid containing neomyicin and dihydrofolate reductase genes was generated containing the βhCG coding sequence fused to antibody B11 at the $CH_3$ domain of the heavy chain (SEQ ID NOs:9 and 10). The resulting plasmid construct was transfected into CHO cells using a standardized protocol (Qiagen Inc, Valencia, Calif.). Transfected cells were selected in media containing the antibiotic G418. Expression was further amplified by growing cells in increasingly higher concentrations of methatrexate. After amplification, the cells were cloned by limiting dilution, and stable clonal lines were used to generate cell banks for further studies. To confirm expression of the βhCG-B11 constructs, Western Blot analysis of proteins run on SDS-PAGE under reducing conditions was performed. This fusion protein was observed to be of the expected molecular weight and to be properly assembled (i.e., to contain both the heavy chain fusion and the light chain). Specifically, the vaccine conjugate and the antibody alone were analyzed by SDS-PAGE using denaturing conditions and detected by Western blot analysis. The blot was then probed separately using goat anti-human IgG heavy and light, and with a mAb (Sigma) specific to the βhCG C-terminal peptide. The results confirmed that the transformed CHO cells specifically expressed the B11-βhCG vaccine conjugate as evidenced by the appropriate size and composition of the fusion product.

Example 2

Production of B11 scfv—βhCG

Design of vaccine conjugate: A second construct was generated by linking the βhCG antigen to a B11 single chain fusion (ScFv), which is a single chain antibody that binds to the human macrophage mannose receptor on dendritic cells and contains the $V_L$ and $V_H$ fragments of the fully human B11 antibody. Linkage was accomplished by covalently attaching the antigen to the carboxy terminus of the B11 ScFv by way of a genetic fusion, as shown in FIG. 1 (referred to as the B11 sfv-βhCG construct).

Recombinant Expression of B11sfv-βhCG Vaccine Conjugate: As shown in FIG. 1, a plasmid was generated containing the B11sfv-βhCG construct (SEQ ID NOs: 11 and 12). The resulting plasmid construct was transfected into mammalian cells using a standardized protocol (Qiagen Inc, Valencia, Calif.). Transfected cells were selected in media containing the antibiotic G418. An ELISA was performed to confirm expression of the B11 sfv-βhCG construct.

Example 3

Functional Characterization of Vaccine Conjugates

Figure 4:
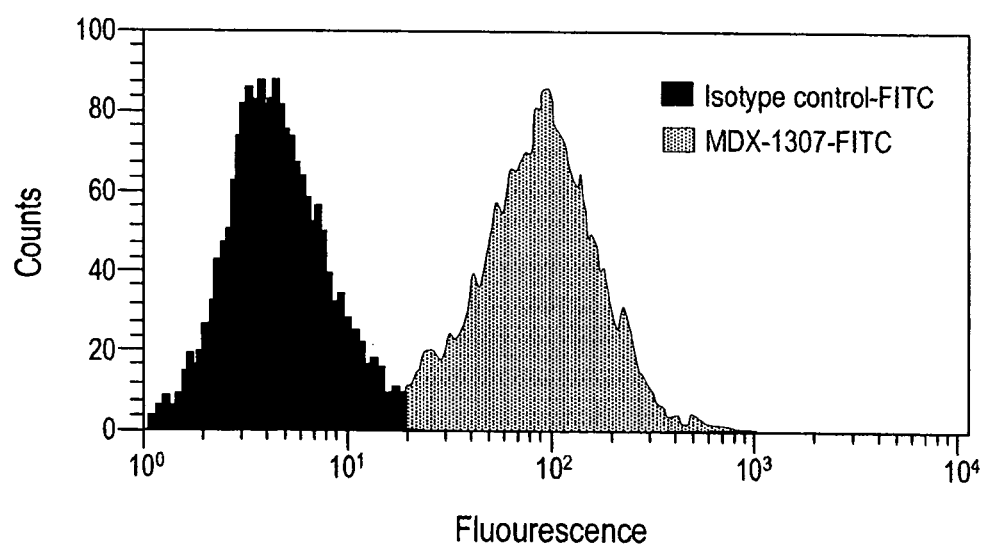
FIG. 4 is a graph based on flow cytometry studies which shows that the βhCG-B11 construct binds specifically to cultured human DC expressing MR.

Antibody-targeted vaccine recognition of its cognate receptor on the APC surface is the first step in this delivery platform. Flow cytometry studies have been used to demonstrate that the βhCG-B11 and B11 sfv-βhCG constructs bind specifically to cultured human DC expressing MR (FIG. 4).

Using the anti-MR antibody as a probe, in situ staining of MR on human dermal DCs and macrophages in section of various human tissues was examined. Human tissue cryosections were stained with anti-MR human antibody B11. DCs present in the dermal layer of the skin were clearly labeled (data not shown) with the B11 antibody. It is noted that there was binding to DCs in the dermal layer of skin. Furthermore, immunohistochemistry performed with the anti-MR B11 HuMAb stained dendritic cells in all tissues tested and showed no unexpected cross-reactivity (results not shown). These studies have been repeated with the βhCG-B11 with identical results.

Example 4

Cross-presentation of the βhCG Antigen/anti-MR Antibody Vaccine Conjugate to T cells The capacity of the βhCG-B11 construct to be processed by DCs for presentation of βhCG antigen to T cells via MHC class I and class II molecules on DCs (cross-presentation) was evaluated. In particular, the βhCG-B11 construct was used to elicit antigen-specific T cells by culturing a pool of normal T cells with DCs that were exposed to the vaccine. The resulting "sensitized" T cells were then analyzed for their activity (proliferation and killing) and specificity. Specificity of the T cells can be demonstrated by comparing the T cell activity in response to target cells that have the βhCG antigen to antigen-negative controls. Cytotoxic T cells (CTL), if present, should kill only those targets that present βhCG related antigen but spare control targets that are either lacking the antigen or presenting an unrelated antigen. Since CTL-mediated antigen recognition always occurs in the context of a given MHC molecule bearing the peptide, blocking the MHC:peptide-CTL interaction with an MHC-specific mAb confirms the class I or class II presentation.

Induction of antigen-specific effector T cells: Dendritic cells were generated from normal donor peripheral blood mononuclear cells (PBMC) by culturing adherent monocytes with 25 ng/ml recombinant human GM-CSF (R&D systems, MN) and 100 ng/ml of recombinant human IL-4 for 5 days. On day 5, DCs were harvested (immature) and resuspended in AIM-V (serum-free) medium. The βhCG-B111 immunoconjugate (20 μg/ml) was added to $1.2 \times 10^6$ DC and incubated for 45 min at 37° C. Antigen-loaded DCs was allowed to mature in the presence of CD40L (Peprotech, NJ; 20 ng/ml) for at least 24 hours. Mature DC ($1 \times 10^6$) were washed once and added to T cells ($2 \times 10^7$; bulk) previously seeded in 24 well plates at $1 \times 10^6$ cells/ml (ratio of DC: T cells, 20). The following culture conditions were employed: addition of 10 ng/ml IL-7 on day 0, followed by 10 ng/ml of IL-10 on day 1 (at 24 hours), and 20 U/ml IL-2 on day 2 (at 48 hours). Restimulation was carried out on days 7, 14 and 21 as before, except that βhCG-B11 concentration was cut by half (10, 5 and 2.5 μg/ml, respectively). T cells were tested for reactivity (either in bulk or with purified T cell sub populations) against $^{51}$Cr-labeled DC loaded with nothing, βhCG-B11, B11sfv-βhCG, or B11. MHC-specificity was ascertained in the presence of HLA-specific mAbs.

Figure 5:
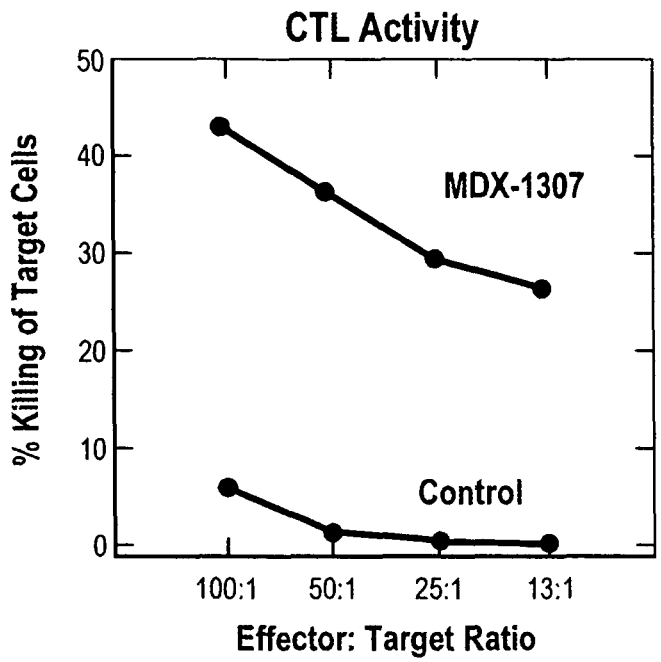
FIG. 5 is a graph showing that the βhCG-B11 construct induces βhCG-specific cytotoxic T cells.

As illustrated in FIG. 5, the βhCG-B11 construct induced βhCG-specific cytotoxic T cells. No killing ensued if the T cells were cultured with targets that do not present βhCG. The target cells used in these experiments were HLA-matched DC treated with the βhCG-B11 construct or control antigens. Target cells treated only with the anti-MR antibody (B11) were not susceptible to the cytotoxic activity, demonstrating that only the antigen portion of the vaccine was able to elicit CTL activity. These results show that the βhCG-B11 construct induces efficient CTL activity and, specifically, the CTL activity is directed towards the βhCG antigen but not the targeting antibody (B11).

Figure 6:
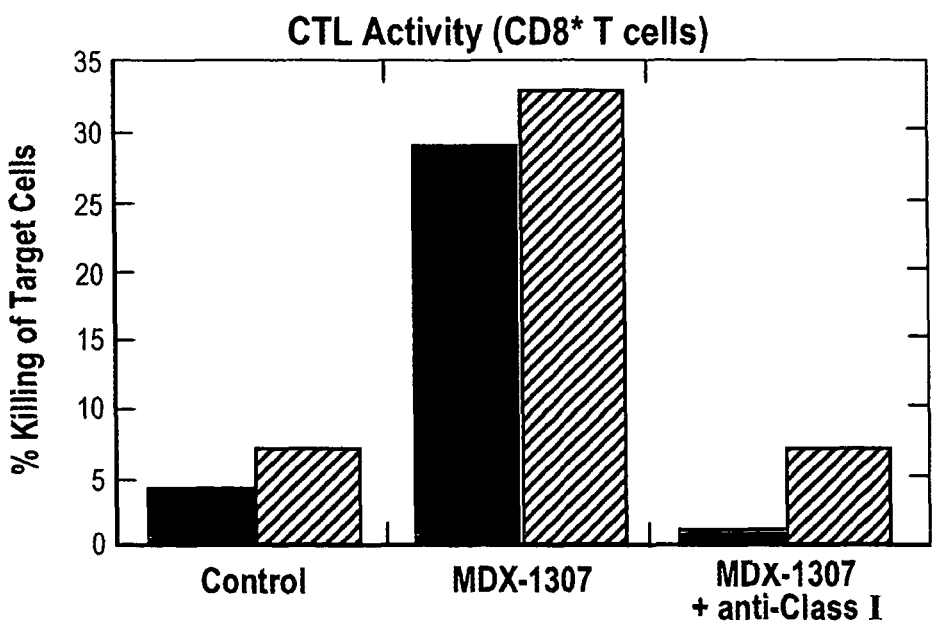
FIG. 6 is a graph showing that the βhCG-B11 construct induces βhCG-specific cytotoxic T cells.

Furthermore, the potent killing of targets presenting βhCG antigen was reproduced with purified CD8$^+$ T cells, which killing was blocked in the presence of anti-MHC class I antibodies (FIG. 6). In particular, the βhCG-B11 construct was used to generate βhCG-specific T cells from peripheral blood mononuclear cells of two donors. CD8$^+$ and CD4$^+$ T cells were purified from bulk cultures using immunomagnetic beads. Cytotoxicity assays were carried out as described above with the effector:target ratio set at 40:1. The target cells (immature DC) were untreated (control) or loaded with the βhCG-B11 construct. To demonstrate MHC Class I specificity, target cell killing was blocked by preincubation with an HLA-specific antibody (W6/32).

Collectively, these data (FIGS. 6 and 7) confirm the ability of the βhCG-B11 construct to induce potent βhCG-specific CTL, and additionally demonstrate that the CTL activity is mediated by CD8$^+$ T cells in an HLA-dependent manner. No killing activity was observed with the purified CD4$^+$ T cells.

Figure 7:
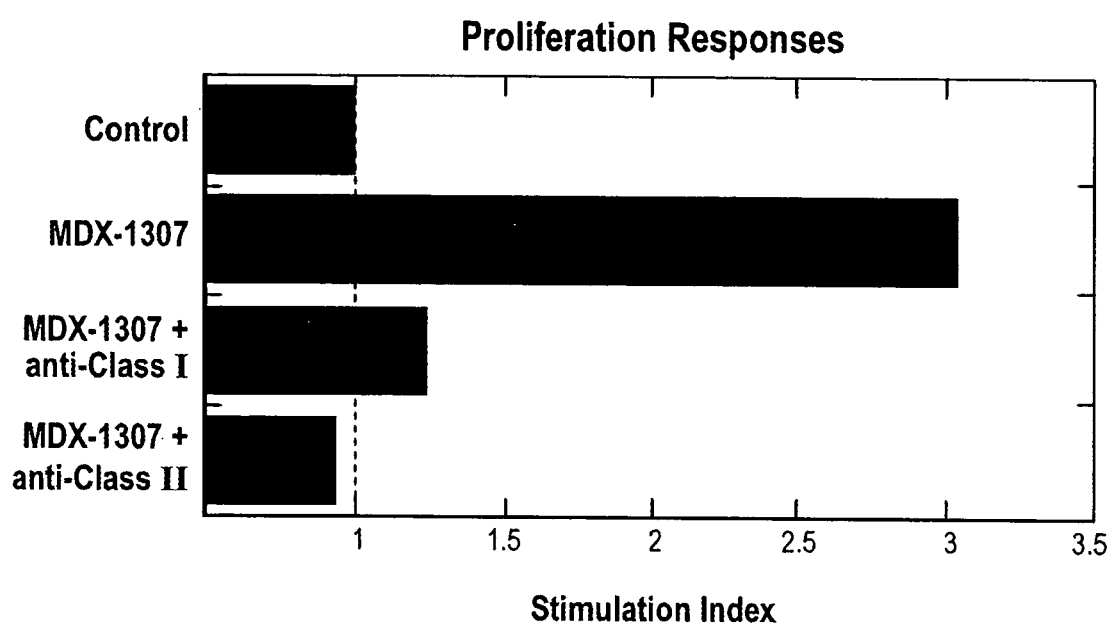
FIG. 7 is a bar graph showing that the βhCG-B11 construct induces T helper response.

As shown in FIG. 7, the βhCG-B11 construct-elicited T cells proliferate in response to the βhCG-B11 construct targeted DC. In particular, DC were treated with the βhCG-B11 construct to generate βhCG-specific T cells from peripheral blood mononuclear cells. T cells from bulk cultures (CD4$^+$ and CD8$^+$ T cells) were tested for proliferation in response to antigen stimulation. T cells were co-cultured with untreated DC (control) or DC loaded with the βhCG-B11 construct with or without HLA blocking antibodies. To measure proliferation, DNA synthesis was analyzed after 5 days of culture using $^3$H-thymidine. The data were expressed as the fold-increase in proliferation (stimulation index) over control. As seen with the CTL activity, no appreciable response was found when the T cells were stimulated by DC alone (i.e., no antigen). DC targeted with only the unconjugated antibody (anti-MR B11 mAb) did not induce proliferation of T cells elicited by the βhCG-B11 construct. The proliferative capacity of the T cells was significantly blocked in the presence of both anti-MHC class I as well as class II-specific mAbs, demonstrating that both CD4$^+$ and CD8$^+$ T cells were responding. These data show that the uptake of the βhCG-B11 construct by DC enables the vaccine to gain access to MHC class I and class II processing pathways, which is consistent with co-localization of MR with MHC compartments.

Example 5

Internalization by DCs of Anti-MR Antibody B11 vs. Internalization by DCs of a Mannosylated Antigen (Inhibition of Clathrin Mediated Internalization)

Immature DCs can take up soluble antigens by pinocytic or receptor mediated endocytic mechanisms (55). The mechanism of antigen internalization determines its intracellular fate and may effect the quality of immune response to it (54, 55, 56). Internalization through the MR has been described as a rapid, clathrin mediated internalization event (57, 58). The MR itself has two putative clathrin targeting sequences within its cytoplasmic tail, and internalization of mannosylated gold particles have localized to clathrin-coated pits by EM (58, 59). Clathrin dependant endocytosis can be specifically disrupted by brief hypertonic shock or K+ depletion (61). In order to determine if mannosylated antigens or B11 bound to the mannose receptor were internalized via clathrin-coated pits, immature DCs were incubated on ice in AIM5 media with or without 400 mM sucrose for 30 min in the presence of either B11 mAb or mannosylated BSA. Cells were then warmed to 37° C. and allowed to internalize for 20 minutes. After being washed and fixed, cells were analyzed by confocal microscopy (data not shown). When B11 was bound to the MR, its uptake was inhibited by hypertonic shock, indicating that its mechanism of internalization was through clathrin coated-pits. Uptake of mannosylated BSA, in contrast, was not inhibited by hypertonic shock, indicating that its mechanism of internalization was not dependent on clathrin coated-pit formation. Even at concentration 20 fold higher than that of B11, surface staining by mannosylated BSA FITC was relatively weak. Subsequent studies revealed that internalized mannosylated BSA FITC co-localized with non-specific, fluid phase tracers, where as vesicles containing internalized B11 excluded the non-specific tracer (data not shown). In contrast to B11'-FITC the uptake of both mannosylated BSA-FITC and the fluid phase tracer was largely blocked by pretreatment with the PI3K inhibitor wortmannin (data not shown). These results indicate that the vast majority of mannosylated BSA was taken up by the immature dendritic cell was through non-specific macropinocytic mechanisms, suggesting that the quality of immune response to the mannosylated antigen may differ greatly from antigen specifically targeted to the MR.

Example 6

Binding of B11sfv-βhCG to DCs

Monocyte-derived DCs were exposed either to B11 sfv-βhCG or βhCG-B 11 in PBS-BSA buffer for 45 minutes at 37° C. and allowed to mature overnight in the presence of CD40L. Harvested DCs were then washed and stained with mouse anti-βhCG followed by goat anti-hu IgG ($F_c$)-PE conjugate. Stained cells were analyzed on a flow cytometer (BD-LSR). Approximately, 10,000 events were collected for each sample. Background autofluorescence and isotype matched antibody staining served as controls. Based on the mean fluorescence intensity (MFI) (data not shown), B11sfv-βhCG binding to MR expressed on DC is similar to that of βhCG-B11.

Example 7

Figure 11:
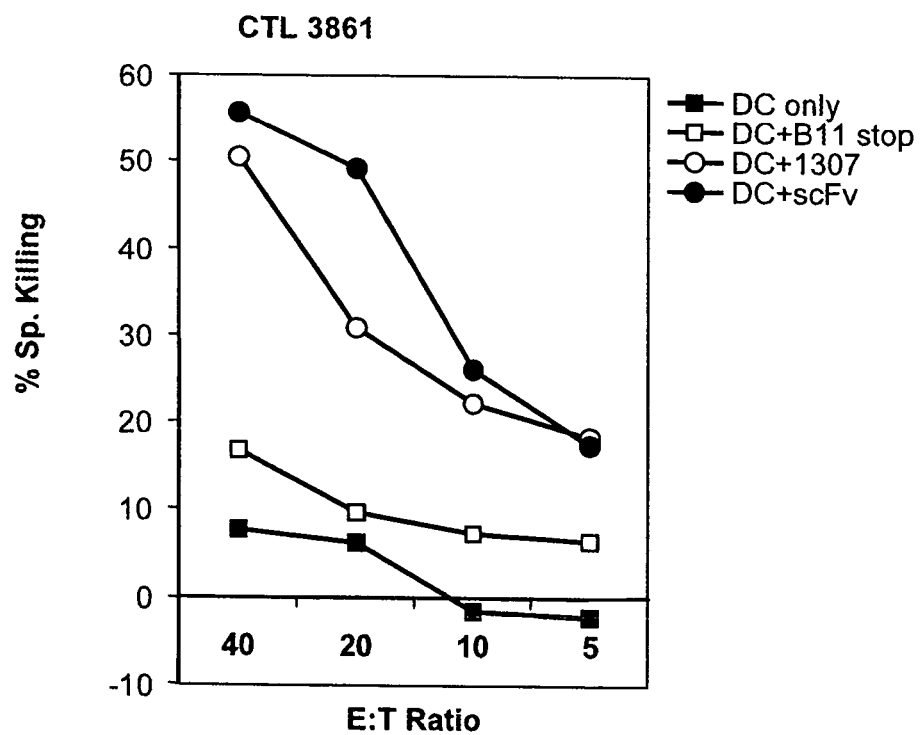
FIG. 11 is a graph showing CTL specific for the βhCG-B11 construct recognize the scFv form of the antigen, B11sfv-βhCG presented by DCs.

CTLs Specific for the βhCG-B11 Construct Recognize the scFv Form of the Antigen (B11sfv-βhCG) Presented by DCs CTL raised to DC-presented βhCG-B11 were tested against autologous DC targets that were exposed to βhCG-B11 and B11sfv-βhCG, while untreated DC or DC exposed to B11 served as controls. Following antigen exposure, targets were labeled with $^{51}$chromium and mixed with CTL in a 4 hour assay that measures release of radioactivity in the supernatant. In this experiment, βhCG-B11-specific T cells recognize two of four targets that present the antigen on MHC class I molecules. No killing of targets ensues when DC lack antigen (FIG. 11). Thus, the uptake of βhCG-B11 by DC likely results in a βhCG-derived T cell epitope recognized by CTL.
Equivalents Those skilled in the art will recognize or be able to ascertain, using no more than routine experimentation, many equivalents of the specific embodiments of the invention described herein. Such equivalents are intended to be encompassed by the following claims.
Incorporation by Reference All patents, pending patent applications and other publications cited herein are hereby incorporated by reference in their entirety.

REFERENCES

1. Steinman, R. M. 1991. The dendritic cell system and its role in immunogenicity. *Annu Rev Immunol.* 9:271.
2. Hart, D. N. 1997. Dendritic cells: unique leukocyte populations which control the primary immune response. *Blood.* 90:3245.
3. Banchereau, J., and R. M. Steinman. 1998. Dendritic cells and the control of immunity. *Nature.* 392:245.
4. Thery C., and S. Amigorena. 2001. The cell biology of antigen presentation in dendritic cells. *Curr Opin Immunol.* 13:45.
5. Hsu F. J., C. Benike, F. Fagnoni, T. M. Liles, D. Czerwinski, B. Taidi, E. G. Engleman, and R. Levy. 1996. Vaccination of patients with B-cell lymphoma using autologous antigen-pulsed dendritic cells. *Nat Med.* 2:52.
6. Kirk C. J., and J. J. Mule. 2000. Gene-modified dendritic cells for use in tumor vaccines. *Hum Gene Ther.* 11:797.
7. Thurner B., I. Haendle, C. Roder, D. Dieckmann, P. Keikavoussi, H. Jonuleit, Bender, C. Maczek, D. Schreiner, P. von den Driesch, E. B. Brocker, R. M. Steinman, A. Enk, E. Kampgen, and G. Schuler. 1999. Vaccination with mage-3A1 peptide-pulsed mature, monocyte-derived dendritic cells expands specific cytotoxic T cells and induces regression of some metastases in advanced stage 1V melanoma. *J Exp Med.* 190:1669.
8. Dallal R. M., and M. T. Lotze. 2000. The dendritic cell and human cancer vaccines. *Curr Opin Immunol.* 12:583.
9. Nair S., J. S. Babu, R. G. Dunham, P. Kanda, R. L. Burke, and B. T. Rouse. 1993. Induction of primary, antiviral cytotoxic, and proliferative responses with antigens administered via dendritic cells. *J. Virol.* 67:4062.
10. Gilboa E. 1999. The makings of a tumor rejection antigen. *Immunity.* 11:263.
11. Fields R. C., K. Shimizu, J. J. Mule. 1998. Murine dendritic cells pulsed with whole tumor lysates mediate potent antitumor immune responses in vitro and in vivo. *Proc Natl Acad Sci USA.* 95:9482.
12. Carayanniotis G., and B. H. Barber. 1987. Adjuvant-free IgG responses induced with antigen coupled to antibodies against class II MHC. *Nature.* 327:59.
13. Snider D. P. and D. M. Segal. 1987. Targeted antigen presentation using crosslinked antibody heteroaggregates. *J. Immunol.* 139:1609.
14. Wang H., M. N. Griffiths, D. R. Burton, and P. Ghazal. 2000. Rapid antibody responses by low-dose, single-step, DCs-targeted immunization. *Proc Natl Acad Sci USA.* 97:847.
15. Jiang W., W. J. Swiggard, C. Heufler, M. Peng, A. Mirza, R. M. Steinman, and M. C. Nussenzweig. 1995. The receptor DEC-205 expressed by DCss and thymic epithelial cells is involved in antigen processing. *Nature.* 375:151.
16. Keler, T., P. M. Guyre, L. A. Vitale, K. Sundarapandiyan, J. G. J. van de Winkel, Y. M. Deo, and R. F. Graziano. 2000. Targeting weak antigens to CD64 elicits potent humoral responses in human CD64 transgenic mice. *J. Immunol.* 165:6738.
17. Regnault, A., D. Lankar, V. Lacabanne, A. Rodriguez, C. Théry, M. Rescigno, T. Saito, S. Verbeek, C. Bonnerot, P. Ricciardi-Castagnoli, and S. Amigorena. 1999. Fcγ Receptor-mediated induction of dendritic cell maturation and major histocompatibility complex class 1-restricted antigen presentation after immune complex internalization. *J. Exp. Med.* 189:371.
18. Wallace P. K., K. Y. Tsang, J. Goldstein, P. Correale, T. M. Jarry, J. Schlom, P. M. Guyre, M. S. Ernstoff, and M. W. Fanger. 2001. Exogenous antigen targeted to FcgammaRI on myeloid cells is presented in association with MHC class I. *J Immunol Methods.* 248:183.
19. Berlyn K. A., B. Schultes, B. Leveugle, A. A. Noujaim, R. B. Alexander, and D. L. Mann. 2001. Generation of CD4 (+) and CD8(+) T lymphocyte responses by dendritic cells armed with PSA/anti-PSA (antigen/antibody) complexes. *Clin Immunol.* 101:276.
20. Dhodapkar K. M., J. Krasovsky, B. Williamson, and M. V. Dhodapkar. 2002. Antitumor monoclonal antibodies enhance cross-presentation of cellular antigens and the generation of myeloma-specific killer T cells by dendritic cells. *J Exp Med.* 195:125.
21. Lonberg N., L. D. Taylor, F. A. Harding, M. Trounstine, K. M. Higgins, S. R. Schramm, C. C. Kuo, R. Mashayekh, K. Wymore, J. G. McCabe, et al. 1994. Antigen-specific human antibodies from mice comprising four distinct genetic modifications. *Nature.* 368:856.

22. Fishwild D. M., S. L. O'Donnell, T. Bengoechea, D. V. Hudson, F. Harding, S. L. Bernhard, D. Jones, R. M. Kay, K. M. Higgins, S. R. Schramm, and N. Lonberg. 1996. High-avidity human IgG kappa monoclonal antibodies from a novel strain of minilocus transgenic mice. *Nat Biotechnol.* 14:845.
23. Kohler G., and C. Milstein. 1975. Continuous cultures of fused cells secreting antibody of predefined specificity. *Nature.* 256:495.
24. Fanger, N. A., D. Voigtlaender, C. Liu, S. Swink, K. Wardwell, J. Fisher, R. F. Graziano, L. C. Pfefferkom, and P. M. Guyre. 1997. Characterization of expression, cytokine regulation, and effector function of the high affinity IgG receptor FcγRI (CD64) expressed on human blood DCss. *J. Immunol.* 158:3090.
25. Gosselin, E. J., K. Wardwell, D. R. Gosselin, N. Alter, J. L. Fisher, and P. M. Guyre. 1992. Enhanced antigen presentation using human Fcα receptor (monocyte/macrophage)-specific immunogens. *J. Immunol.* 149:3477.
26. Stahl P. D. 1992. The mannose receptor and other macrophage lectins. *Curr Opin Immunol.* 4:49.
27. Uccini S., M. C. Sirianni, L. Vincenzi, S. Topino, A. Stoppacciaro, I. Lesnoni La Parola, M. Capuano, C. Masini, D. Cerimele, M. Cella, A. Lanzavecchia, P. Allavena, Mantovani, C. D. Baroni, and L. P. Ruco. 1997. Kaposi's sarcoma cells express the macrophage-associated antigen mannose receptor and develop in peripheral blood cultures of Kaposi's sarcoma patients. *Am J Pathol.* 150: 929.
28. Magnusson S., and T. Berg. 1993. Endocytosis of ricin by rat liver cells in vivo and in vitro is mainly mediated by mannose receptors on sinusoidal endothelial cells. *Biochem J.* 291:749.
29. Noorman F., E. A. Braat, M. Barrett-Bergshoeff, E. Barbe, A. van Leeuwen, J. Lindeman, and D. C. Rijken. 1997. Monoclonal antibodies against the human mannose receptor as a specific marker in flow cytometry and immunohistochemistry for macrophages. *J Leukoc Biol.* 61:63.
30. Nobes C, Marsh M. 2000. Dendritic cells: new roles for Cdc42 and Rac in antigen uptake? Curr Biol. 10:20.
31. Lanzavecchia A. 1996. Mchanisms of antigen uptake for presentation. Curr Opin Immunol. 8:3.
32. Harris J., Werling D., Hope J. C., Taylor G., Howard C. J. 2002. Caveolea and caveolin in immune cells: distribution and functions. Trends Immunol. 23:3.
33. Apostolopoulos V., McKenzie I. F. 2001. Role of the mannose receptor in the immune response. Curr Mol Med. 1:4.
34. East L., Isacke C. M. 2002. The mannose receptor family. Biochim Biophys Acta. 1572:2-3.
35. Lew D. B., Songu-Mize E., Pontow S. E., Stahl P. D., Rattazzi M. C. 1994. A mannose receptor mediates mannosyl-rich glycoprotein-induced mitogenesis in bovine airway smooth muscle cells. J Clin Invest. 94:5.
36. Mueller A., Kelly E., Stramge P. G. 2002. Pathways for internalization and recycling of the chemokine receptor CCR5. Blood. 99:3.
37. Taylor M. E., J. T. Conary, M. R. Lennartz, P. D. Stahl, and K. Drickamer. 1990. Primary structure of the mannose receptor contains multiple motifs resembling carbohydrate-recognition domains. *J Biol. Chem.* 265:12156.
38. Taylor M. E. 2001. Structure and function of the macrophage mannose receptor. *Results Probl Cell Differ.* 33:105.
39. Simpson D. Z., P. G. Hitchen, E. L. Elmhirst, and M. E. Taylor. 1999. Multiple interactions between pituitary hormones and the mannose receptor. *Biochem J.* 343:403.
40. Irjala H., E. L. Johansson, R. Grenman, K. Alanen, M. Salmi, and S. Jalkanen. 2001. Mannose receptor is a novel ligand for L-selectin and mediates lymphocyte binding to lymphatic endothelium. *J Exp Med.* 194:1033.
41. Lee, S. J., S. Evers, D. Roeder, A. F. Parlow, J. Risteli, L. Risteli, Y. C. Lee, T. Feizi, H. Langen, and M. C. Nussenzweig. Mannose receptor-mediated regulation of serum glycoprotein homeostasis. *Science* 295:1898.
42. Condaminet B., J. Peguet-Navarro, P. D. Stahl, C. Dalbiez-Gauthier, D. Schmitt, and O. Berthier-Vergnes. 1998. Human epidermal Langerhans cells express the mannose-fucose binding receptor. *Eur J Immunol.* 28:3541.
43. Reis e Sousa C., P. D. Stahl, and J. M. Austyn. 1993. Phagocytosis of antigens by Langerhans cells in vitro. *J Exp Med.* 178:509.
44. Mommaas A. M., A. A. Mulder, R. Jordens, C. Out, M. C. Tan, P. Cresswell, P. M. Kluin, and F. Koning. 1999. Human epidermal Langerhans cells lack functional mannose receptors and a fully developed endosomal/lysosomal compartment for loading of HLA class II molecules. *Eur J Immunol.* 29:571.
45. Lohse A. W., P. A. Knolle, K. Bilo, A. Uhrig, C. Waldmann, M. Ibe, E. Schmitt, G. Gerken, K. H. Meyer Zum Buschenfelde. 1996. Antigen-presenting function and B7 expression of murine sinusoidal endothelial cells and Kupffer cells. Gastroenterology. 110:1175.
46. Tan M. C., A. M. Mommaas, J. W. Drijfhout, R. Jordens, J. J. Onderwater, D. Verwoerd, A. A. Mulder, A. N. van der Heiden, D. Scheidegger, L. C. Oomen, T. H. Ottenhoff, A. Tulp, J. J. Neefjes, and F. Koning. 1997. Mannose receptor-mediated uptake of antigens strongly enhances HLA class II-restricted antigen presentation by cultured DCss. *Eur J Immunol.* 27:2426.
47. Engering A. J., M. Cella, D. M. Fluitsma, E. C. Hoefsmit, A. Lanzavecchia, and J. Pieters. 1997. Mannose receptor mediated antigen uptake and presentation in human DCss. *Adv Exp Med Biol.* 417:183.
48. Apostolopoulos V., G. A. Pietersz, S. Gordon, L. Martinez-Pomares, and I. F. McKenzie. 2000. Aldehyde-mannan antigen complexes target the MHC class I antigen-presentation pathway. *Eur J Immunol.* 30:1714.
49. Prigozy T. I., P. A. Sieling, D. Clemens, P. L. Stewart, S. M. Behar, S. A. Porcelli, M. B. Brenner, R. L. Modlin, and M. Kronenberg. 1997. The mannose receptor delivers lipoglycan antigens to endosomes for presentation to T cells by CD1b molecules. *Immunity.* 6:187.
50. Apostolopoulos V., B. E. Loveland, G. A. Pietersz, and I. F. McKenzie. 1995. CTL in mice immunized with human mucin 1 are MHC-restricted. *J. Immunol.* 155:5089.
51. Dhodapkar M. V., R. M. Steinman, J. Krasovsky, C. Munz, and N. Bhardwaj. 2001. Antigen-specific inhibition of effector T cell function in humans after injection of immature dendritic cells. *J Exp Med.* 193:233.
52. Hawiger D., K. Inaba, Y. Dorsett, M. Guo, K. Mahnke, M. Rivera, J. V. Ravetch, R. M. Steinman, and M. C. Nussenzweig. 2001. Dendritic cells induce peripheral T cell unresponsiveness under steady state conditions in vivo. *J Exp Med.* 194:769.
53. Wallace, P. K., Romet-Lemonne, J. L., Chokri, M., Fanger, M. W., and Fadul, C. E. Production of macrophage activated killer cells for in vivo targeting to glioblastoma with a bispecific antibody to FcγRI and EGF receptor, Cancer Immunol. Immunother. 49: 493-503, 2000.
54. Nobes C, Marsh M. Dendritic cells: new roles for Cdc42 and Rac in antigen uptake? Curr Biol. 2000 Oct. 19;10(20): R739-41.

55. Lanzavecchia A. Mechanisms of antigen uptake for presentation. Curr Opin Immunol. 1996 June; 8(3):348-54.
57. Harris J, Werling D, Hope J C, Taylor G, Howard C J. Caveolae and caveolin in immune cells: distribution and functions. Trends Immunol. 2002 March; 23(3):158-64
58. Apostolopoulos V, McKenzie I F Role of the mannose receptor in the immune response Curr Mol Med. 2001 September; 1 (4):469-74. Review PMID: 11899091 [PubMed—indexed for MEDLINE]
59. East L, Isacke C M. The mannose receptor family Biochim Biophys Acta. 2002 Sep. 19; 1572(2-3):364-86.
60. Lew D B, Songu-Mize E, Pontow S E, Stahl P D, Rattazzi M C. A mannose receptor mediates mannosyl-rich glycoprotein-induced mitogenesis in bovine airway smooth muscle cells J Clin Invest. 1994 November; 94(5):1855-63
61. Mueller A, Kelly E, Strange P G. Related Articles, Links Pathways for internalization and recycling of the chemokine receptor CCR5 Blood. 2002 Feb. 1; 99(3):785-91.
62. Cohen, B. E., A. S. Rosenthal, and W. E. Paul. 1973. Antigen-macrophage interaction. II. Relative roles of cytophilic antibody and other membrane sites. J. Immunol. 111:820.
63. Wemersson, S., Karlsson M. C. I., Dahlström J., Mattsson R., Verbeek J. S., and Heyman B. 1999. IgG-mediated enhancement of antibody responses is low in Fc receptor g δ chain-deficient mice and increased in FcγRII-deficient mice. J. Immunol. 163:618.
64. Regnault, A., D. Lankar, V. Lacabanne, A. Rodriguez, C. Théry, M. Rescigno, T. Saito, S. Verbeek, C. Bonnerot, P. Ricciardi-Castagnoli, and S. Amigorena. 1999. Fcg δ Receptor-mediated induction of dendritic cell maturation and major histocompatibility complex class1-restricted antigen presentation after immune complex internalization. J. Exp. Med. 189:371
65. Wallace P. K., K. Y. Tsang, J. Goldstein, P. Correale, T. M. Jarry, J. Schlom, P. M. Guyre, M. S. Ernstoff, and M. W. Fanger. 2001. Exogenous antigen targeted to FcgammaRI on myeloid cells is presented in association with MHC class I. J Immunol Methods. 248:183.
66. Snider D. P. and D. M. Segal. 1987. Targeted antigen presentation using crosslinked antibody heteroaggregates. J. Immunol. 139:1609.
67. Carayanniotis G., and B. H. Barber. 1987. Adjuvant-free IgG responses induced with antigen coupled to antibodies against class II MHC. Nature. 327:59.
68. Taylor M. E. 2001. Structure and function of the macrophage mannose receptor. Results Probl Cell Differ. 33:105.
69. Fanger, N. A., D. Voigtlaender, C. Liu, S. Swink, K. Wardwell, J. Fisher, R. F. Graziano, L. C. Pfefferkom, and P. M. Guyre. 1997. Characterization of expression, cytokine regulation, and effector function of the high affinity IgG receptor Fcgδ RI (CD64) expressed on human blood DCs. J. Immunol. 158:3090.
70. Treml, J. F., Deo, M. D., Wallace, P. K., and T. Keler. A Mannose receptor-specific human antibody for delivery of antigens to dendritic cells. Prepared for submission to J. Leuk. Biol. 2003.
71. Keler, T., P. M. Guyre, L. A. Vitale, K. Sundarapandiyan, J. G. J. van de Winkel, Y. M. Deo, and R. F. Graziano. 2000. Targeting weak antigens to CD64 elicits potent humoral responses in human CD64 transgenic mice. J. Immunol. 165:6738.
72. Guyre C A, Barreda M E, Swink S L, Fanger M W. 2001. Colocalization of Fc gamma RI-targeted antigen with class I MHC: implications for antigen processing. J Immunol 166(4):2469-78.
73. Triozzi, P. L. and V. Stevens. 1999. Human Chorionic gonadotropin as a target for cancer vaccines (Review). Oncology reports 6: 7-17.
74. Louchimo, J., Carpelan-Holmstrom, M., Alfthan, H., Stenman, U. H., Jarvinen, H. J., Haglund, C. 2002. Serum hCGbδ, δ δ CA 72-4, and CEA are independent prognostic factors in colorectal cancer. Int. J. Can. 101:545-548.
75. Hotakainen, K., Ljungberg, B., Paju, A., Alfthan, H., and U-H Stenman. 2002. The free b-subunit of human chorionic gonadotropin as a prognostic factor in renal cell carcinoma. British J. of Can. 86:185-189.
76. Heijnen, I. A., M. J. van Vugt, N. A. Fanger, R. F. Graziano, T. P. de Wit, F. M. Hofhuis, P. M. Guyre, P. J. Capel, J. S. Verbeek, and J. G. van de Winkel. 1996. Antigen targeting to myeloid-specific human Fcgδ RI/CD64 triggers enhanced antibody responses in transgenic mice. J. Clin. Invest. 97:331.
77. WO 91/00360
78. U.S. Pat. No. 4,950,480
79. Snider, et al. (1990) J. of Exp. Med. 171:1957-1963.
80. Shen et al. J. of Immunol. 137(11):3378-3382.
81. Snider and Segal (1989) J. of Immunol. 143(1):59-65.
82. U.S. Pat. No. 4,954,617
83. Snider and Segal (1987) J. Immunology 139:1609-1616
84. Kawamura and Berzofsky (1986) J. of Immunol. 136(1): 58-65.

We claim:

1. A composition formulated without an adjuvant or immunostimulatory agent comprising a molecular conjugate of a monoclonal antibody that binds to human macrophage mannose receptor (MMR) linked to βhCG, wherein the molecular conjugate is internalized and processed by APCs, such that a T cell-mediated immune response is generated against βhCG.

2. The composition of claim 1, wherein βhCG is linked to the antibody covalently, non-covalently, or recombinantly.

3. The composition of claim 1, wherein the antibody and βhCG are expressed together as a single recombinant fusion protein.

4. The composition of claim 1, wherein the antibody is selected from the group consisting of human, humanized and chimeric antibodies.

5. The composition of claim 1, wherein the antibody is selected from the group consisting of a whole antibody, an Fab fragment and a single chain antibody.

6. The composition of claim 1, wherein the conjugate is a recombinant fusion protein.

7. The composition of claim 1, wherein the antibody comprises a heavy chain variable region comprising FR1, CDR1, FR2, CDR2, FR3, CDR3 and FR4 sequences and a light chain variable region comprising FR1, CDR1, FR2, CDR2, FR3, CDR3 and FR4 sequences, wherein:

(a) the heavy chain variable region CDR3 sequence comprises SEQ ID NO: 15;

(b) the light chain variable region CDR3 sequence comprises SEQ ID NO: 18;

(c) the heavy chain variable region CDR2 sequence comprises SEQ ID NO: 14;

(d) the human light chain variable region CDR2 sequence comprises SEQ ID NO:17;

(e) the heavy chain variable region CDR1 sequence comprises SEQ ID NO:13; and (f) the light chain variable region CDR1 sequence comprises SEQ ID NO:16.

8. The composition of claim 1, wherein the antibody comprises a heavy chain variable region comprising the amino acid sequence shown in SEQ ID NO:4.

9. The composition of claim 1, wherein the antibody comprises a light chain variable region comprising the amino acid sequence shown in SEQ ID NO:8.

10. A composition formulated without an adjuvant or immunostimulatory agent comprising a molecular conjugate of an antibody heavy chain that binds to human MMR and an antibody light chain that binds to human MMR, wherein one of the chains is linked to βhCG, and wherein the molecular conjugate is internalized and processed by APCs, such that a T cell-mediated immune response is generated against βhCG.

11. A composition formulated without an adjuvant or immunostimulatory agent comprising a molecular conjugate comprising the amino acid sequence shown in SEQ ID NO:12, wherein the molecular conjugate is internalized and processed by APCs, such that a T cell-mediated immune response is generated against βhCG.

12. The composition of claim 1, wherein the T cell response is mediated by cytotoxic T cells.

13. The composition of claim 1, wherein the T cell response is mediated by both $CD4^+$and $CD8^+$T cells.

14. The composition of claim 1, wherein the T cell response is induced through both MHC class I and MHC class II pathways.

* * * * *

UNITED STATES PATENT AND TRADEMARK OFFICE
CERTIFICATE OF CORRECTION

PATENT NO. : 9,259,459 B2
APPLICATION NO. : 10/903191
DATED : February 16, 2016
INVENTOR(S) : Keler et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1228 days.

Signed and Sealed this
Twenty-first Day of June, 2016

Michelle K. Lee
*Director of the United States Patent and Trademark Office*

SEQUENCE LISTING

```
<160> NUMBER OF SEQ ID NOS: 32

<210> SEQ ID NO 1
<211> LENGTH: 1407
<212> TYPE: DNA
<213> ORGANISM: Homo sapiens

<400> SEQUENCE: 1
atgggatgga gctgtatcat cctgttcctc gtggccacag caaccggtgt ccactctgag      60
gtgcagctgg tgcagtctgg agcagaggtg aaaaagcccg gggagtctct gaggatctcc     120
tgtaagggtt ctggagacag ttttaccacc tactggatcg gctgggtgcg ccagatgccc     180
gggaaaggcc tggagtggat ggggatcatc tatcctggtg actctgatac catatacagc     240
ccgtccttcc aaggccaggt caccatctca gccgacaagt ccatcagcac cgcctacctg     300
cagtggagca gcctgaaggc ctcggacacc gccatgtatt actgtacgag aggggaccgg     360
```

```
ggcgttgact actggggcca gggaaccctg gtcaccgtct cctcagctag caccaagggc    420
ccatcggtct tcccctggc accctcctcc aagagcacct ctgggggcac agcggccctg    480
ggctgcctgg tcaaggacta cttccccgag ccggtgacgg tgtcgtggaa ctcaggcgcc    540
ctgaccagcg gcgtgcacac cttcccggct gtcctacagt cctcaggact ctactccctc    600
agcagcgtgg tgaccgtgcc ctccagcagc ttgggcaccc agacctacat ctgcaacgtg    660
aatcacaagc ccagcaacac caaggtggac aagaaagttg agcccaaatc ttgtgacaaa    720
actcacacat gcccaccgtg cccagcacct gaactcctgg ggggaccgtc agtcttcctc    780
ttccccccaa aacccaagga caccctcatg atctcccgga cccctgaggt cacatgcgtg    840
gtggtggacg tgagccacga agaccctgag gtcaagttca actggtacgt ggacggcgtg    900
gaggtgcata atgccaagac aaagccgcgg gaggagcagt acaacagcac gtaccgtgtg    960
gtcagcgtcc tcaccgtcct gcaccaggac tggctgaatg gcaaggagta caagtgcaag   1020
gtctccaaca aagccctccc agcccccatc gagaaaacca tctccaaagc caaagggcag   1080
ccccgagaac cacaggtgta caccctgccc ccatcccggg atgagctgac caagaaccag   1140
gtcagcctga cctgcctggt caaaggcttc tatcccagcg acatcgccgt ggagtgggag   1200
agcaatgggc agccggagaa caactacaag accacgcctc ccgtgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaaggctc gagctga                                        1407

<210> SEQ ID NO 2
<211> LENGTH: 468
<212> TYPE: PRT
<213> ORGANISM: Homo sapiens

<400> SEQUENCE: 2

Met Gly Trp Ser Cys Ile Ile Leu Phe Leu Val Ala Thr Ala Thr Gly
  1               5                  10                  15

Val His Ser Glu Val Gln Leu Val Gln Ser Gly Ala Glu Val Lys Lys
             20                  25                  30

Pro Gly Glu Ser Leu Arg Ile Ser Cys Lys Gly Ser Gly Asp Ser Phe
         35                  40                  45

Thr Thr Tyr Trp Ile Gly Trp Val Arg Gln Met Pro Gly Lys Gly Leu
     50                  55                  60

Glu Trp Met Gly Ile Ile Tyr Pro Gly Asp Ser Asp Thr Ile Tyr Ser
 65                  70                  75                  80

Pro Ser Phe Gln Gly Gln Val Thr Ile Ser Ala Asp Lys Ser Ile Ser
                 85                  90                  95

Thr Ala Tyr Leu Gln Trp Ser Ser Leu Lys Ala Ser Asp Thr Ala Met
            100                 105                 110

Tyr Tyr Cys Thr Arg Gly Asp Arg Gly Val Asp Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
```

```
                    180               185               190
        Gln Ser Ser Gly Leu Tyr Ser Leu Ser Ser Val Val Thr Val Pro Ser
                195               200               205

Ser Ser Leu Gly Thr Gln Thr Tyr Ile Cys Asn Val Asn His Lys Pro
                210               215               220

Ser Asn Thr Lys Val Asp Lys Lys Val Glu Pro Lys Ser Cys Asp Lys
        225               230               235               240

Thr His Thr Cys Pro Pro Cys Pro Ala Pro Glu Leu Leu Gly Gly Pro
                        245               250               255

Ser Val Phe Leu Phe Pro Pro Lys Pro Lys Asp Thr Leu Met Ile Ser
                        260               265               270

Arg Thr Pro Glu Val Thr Cys Val Val Val Asp Val Ser His Glu Asp
                    275               280               285

Pro Glu Val Lys Phe Asn Trp Tyr Val Asp Gly Val Glu Val His Asn
                290               295               300

Ala Lys Thr Lys Pro Arg Glu Glu Gln Tyr Asn Ser Thr Tyr Arg Val
        305               310               315               320

Val Ser Val Leu Thr Val Leu His Gln Asp Trp Leu Asn Gly Lys Glu
                        325               330               335

Tyr Lys Cys Lys Val Ser Asn Lys Ala Leu Pro Ala Pro Ile Glu Lys
                        340               345               350

Thr Ile Ser Lys Ala Lys Gly Gln Pro Arg Glu Pro Gln Val Tyr Thr
                    355               360               365

Leu Pro Pro Ser Arg Asp Glu Leu Thr Lys Asn Gln Val Ser Leu Thr
                370               375               380

Cys Leu Val Lys Gly Phe Tyr Pro Ser Asp Ile Ala Val Glu Trp Glu
        385               390               395               400

Ser Asn Gly Gln Pro Glu Asn Asn Tyr Lys Thr Thr Pro Pro Val Leu
                        405               410               415

Asp Ser Asp Gly Ser Phe Phe Leu Tyr Ser Lys Leu Thr Val Asp Lys
                        420               425               430

Ser Arg Trp Gln Gln Gly Asn Val Phe Ser Cys Ser Val Met His Glu
                    435               440               445

Ala Leu His Asn His Tyr Thr Gln Lys Ser Leu Ser Leu Ser Pro Gly
                450               455               460

Lys Gly Ser Ser
        465

<210> SEQ ID NO 3
<211> LENGTH: 348
<212> TYPE: DNA
<213> ORGANISM: Homo sapiens

<400> SEQUENCE: 3
gaggtgcagc tggtgcagtc tggagcagag gtgaaaaagc ccggggagtc tctgaggatc      60
tcctgtaagg gttctggaga cagttttacc acctactgga tcggctgggt gcgccagatg     120
cccgggaaag gcctggagtg gatggggatc atctatcctg gtgactctga taccatatac     180
agcccgtcct tccaaggcca ggtcaccatc tcagccgaca gtccatcagc caccgcctac     240
ctgcagtgga gcagcctgaa ggcctcggac accgccatgt attactgtac gagaggggac     300
cggggcgttg actactgggg ccagggaacc ctggtcaccg tctcctca                  348

<210> SEQ ID NO 4
<211> LENGTH: 116
```

```
<212> TYPE: PRT
<213> ORGANISM: Homo sapiens

<400> SEQUENCE: 4

Glu Val Gln Leu Val Gln Ser Gly Ala Glu Val Lys Lys Pro Gly Glu
 1               5                  10                  15

Ser Leu Arg Ile Ser Cys Lys Gly Ser Gly Asp Ser Phe Thr Thr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Ile Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Thr Arg Gly Asp Arg Gly Val Asp Tyr Trp Gly Gln Gly Thr Leu Val
            100                 105                 110

Thr Val Ser Ser
        115

<210> SEQ ID NO 5
<211> LENGTH: 702
<212> TYPE: DNA
<213> ORGANISM: Homo sapiens

<400> SEQUENCE: 5
atgggatgga gctgtatcat cctgttcctc gtggccacag caaccggtgt ccactccgac      60
atccagatga cccagtctcc atcctcactg tctgcatctg taggagacag agtcaccatc     120
acttgtcggg cgagtcaggg tattagcagg tggttagcct ggtatcagca gaaaccagag     180
aaagccccta gtccctgat  ctatgctgca tccagtttgc aaagtggggt cccatcaagg     240
ttcagcggca gtggatctgg gacagatttc actctcacca tcagcggcct gcagcctgaa     300
gattttgcaa cttattactg ccaacagtat aatagttacc tcggacgtt  cggccaaggg     360 accaaggtgg aaatcaaacg tacggtggcg gcgccatctg tcttcatctt cccgccatct     420
gatgagcagt tgaaatctgg aactgcctct gttgtgtgcc tgctgaataa cttctatccc     480
agagaggcca agtacagtg  gaaggtggat aacgccctcc aatcgggtaa ctcccaggag     540
agtgtcacag agcaggacag caaggacagc acctacagcc tcagcagcac cctgacgctg     600
agcaaagcag actacgagaa acacaaagtc tacgcctgcg aagtcaccca tcagggcctg     660
agctcgcccg tcacaaagag cttcaacagg ggagagtgtt ag                       702

<210> SEQ ID NO 6
<211> LENGTH: 233
<212> TYPE: PRT
<213> ORGANISM: Homo sapiens

<400> SEQUENCE: 6

Met Gly Trp Ser Cys Ile Ile Leu Phe Leu Val Ala Thr Ala Thr Gly
 1               5                  10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Gly Ile
        35                  40                  45

Ser Arg Trp Leu Ala Trp Tyr Gln Gln Lys Pro Glu Lys Ala Pro Lys
```

```
            50                  55                  60
Ser Leu Ile Tyr Ala Ala Ser Ser Leu Gln Ser Gly Val Pro Ser Arg
 65                  70                  75                  80

Phe Ser Gly Ser Gly Ser Gly Thr Asp Phe Thr Leu Thr Ile Ser Gly
                 85                  90                  95

Leu Gln Pro Glu Asp Phe Ala Thr Tyr Tyr Cys Gln Gln Tyr Asn Ser
            100                 105                 110

Tyr Pro Arg Thr Phe Gly Gln Gly Thr Lys Val Glu Ile Lys Arg Thr
            115                 120                 125

Val Ala Ala Pro Ser Val Phe Ile Phe Pro Pro Ser Asp Glu Gln Leu
            130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230
```

```
<210> SEQ ID NO 7
<211> LENGTH: 321
<212> TYPE: DNA
<213> ORGANISM: Homo sapiens

<400> SEQUENCE: 7
gacatccaga tgacccagtc tccatcctca ctgtctgcat ctgtaggaga cagagtcacc    60
atcacttgtc gggcgagtca gggtattagc aggtggttag cctggtatca gcagaaacca   120
gagaaagccc ctaagtccct gatctatgct gcatccagtt tgcaaagtgg ggtcccatca   180
aggttcagcg gcagtggatc tgggacagat ttcactctca ccatcagcgg cctgcagcct   240
gaagattttg caacttatta ctgccaacag tataatagtt accctcggac gttcggccaa   300
gggaccaagg tggaaatcaa a                                             321
```

```
<210> SEQ ID NO 8
<211> LENGTH: 107
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Arg Trp
             20                  25                  30

Leu Ala Trp Tyr Gln Gln Lys Pro Glu Lys Ala Pro Lys Ser Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Gly Leu Gln Pro
 65                  70                  75                  80

Glu Asp Phe Ala Thr Tyr Tyr Cys Gln Gln Tyr Asn Ser Tyr Pro Arg
```

85                  90                  95
Thr Phe Gly Gln Gly Thr Lys Val Glu Ile Lys
            100                 105

<210> SEQ ID NO 9
<211> LENGTH: 1842
<212> TYPE: DNA
<213> ORGANISM: Homo sapiens

<400> SEQUENCE: 9

| | | | | | |
|---|---|---|---|---|---|
| atgggatgga | gctgtatcat | cctgttcctc | gtggccacag | caaccggtgt | ccactctgag | 60 |
| gtgcagctgg | tgcagtctgg | agcagaggtg | aaaaagcccg | ggagtctct | gaggatctcc | 120 |
| tgtaagggtt | ctggagacag | ttttaccacc | tactggatcg | gctgggtgcg | ccagatgccc | 180 |
| gggaaaggcc | tggagtggat | ggggatcatc | tatcctggtg | actctgatac | catatacagc | 240 |
| ccgtccttcc | aaggccaggt | caccatctca | gccgacaagt | ccatcagcac | cgcctacctg | 300 |
| cagtggagca | gcctgaaggc | ctcggacacc | gccatgtatt | actgtacgag | agggaccgg | 360 |
| ggcgttgact | actggggcca | gggaaccctg | gtcaccgtct | cctcagctag | caccaagggc | 420 |
| ccatcggtct | tccccctggc | accctcctcc | aagagcacct | ctgggggcac | agcggccctg | 480 |
| ggctgcctgg | tcaaggacta | cttccccgag | ccggtgacgg | tgtcgtggaa | ctcaggcgcc | 540 |
| ctgaccagcg | gcgtgcacac | cttcccggct | gtcctacagt | cctcaggact | ctactccctc | 600 |
| agcagcgtgg | tgaccgtgcc | ctccagcagc | ttgggcaccc | agacctacat | ctgcaacgtg | 660 |
| aatcacaagc | ccagcaacac | caaggtggac | aagaaagttg | agcccaaatc | ttgtgacaaa | 720 |
| actcacacat | gcccaccgtg | cccagcacct | gaactcctgg | ggggaccgtc | agtcttcctc | 780 |
| ttccccccaa | aacccaagga | caccctcatg | atctcccgga | cccctgaggt | cacatgcgtg | 840 |
| gtggtggacg | tgagccacga | agaccctgag | gtcaagttca | actggtacgt | ggacggcgtg | 900 |
| gaggtgcata | atgccaagac | aaagccgcgg | gaggagcagt | acaacagcac | gtaccgtgtg | 960 |
| gtcagcgtcc | tcaccgtcct | gcaccaggac | tggctgaatg | gcaaggagta | caagtgcaag | 1020 |
| gtctccaaca | aagccctccc | agcccccatc | gagaaaacca | tctccaaagc | caaagggcag | 1080 |
| ccccgagaac | cacaggtgta | caccctgccc | ccatcccggg | atgagctgac | caagaaccag | 1140 |
| gtcagcctga | cctgcctggt | caaaggcttc | tatcccagcg | acatcgccgt | ggagtgggag | 1200 |
| agcaatgggc | agccggagaa | caactacaag | accacgcctc | ccgtgctgga | ctccgacggc | 1260 |
| tccttcttcc | tctacagcaa | gctcaccgtg | gacaagagca | ggtggcagca | ggggaacgtc | 1320 |
| ttctcatgct | ccgtgatgca | tgaggctctg | cacaaccact | acacgcagaa | gagcctctcc | 1380 |
| ctgtctccgg | gtaaaggctc | gagctccaag | gagccgcttc | ggccacggtg | ccgccccatc | 1440 |
| aatgccaccc | tggctgtgga | aaggagggc | tgccccgtgt | gcatcaccgt | caacaccacc | 1500 |
| atctgtgccg | gctactgccc | caccatgacc | cgcgtgctgc | aggggtcct | gccggccctg | 1560 |
| cctcaggtgg | tgtgcaacta | ccgcgatgtg | cgcttcgagt | ccatccggct | ccctggctgc | 1620 |
| ccgcgcggcg | tgaaccccgt | ggtctcctac | gccgtggctc | tcagctgtca | atgtgcactc | 1680 |
| tgccgccgca | gcaccactga | ctgcggggt | cccaaggacc | accccttgac | ctgtgatgac | 1740 |
| ccccgcttcc | aggactcctc | ttcctcaaag | gcccctcccc | cagccttcc | aagtccatcc | 1800 |
| cgactcccgg | ggccctcgga | caccccgatc | ctcccacaat | aa | | 1842 |

<210> SEQ ID NO 10
<211> LENGTH: 613
<212> TYPE: PRT

-continued

<213> ORGANISM: Homo sapiens

<400> SEQUENCE: 10

Met Gly Trp Ser Cys Ile Ile Leu Phe Leu Val Ala Thr Ala Thr Gly
1               5                   10                  15

Val His Ser Glu Val Gln Leu Val Gln Ser Gly Ala Glu Val Lys Lys
            20                  25                  30

Pro Gly Glu Ser Leu Arg Ile Ser Cys Lys Gly Ser Gly Asp Ser Phe
        35                  40                  45

Thr Thr Tyr Trp Ile Gly Trp Val Arg Gln Met Pro Gly Lys Gly Leu
    50                  55                  60

Glu Trp Met Gly Ile Ile Tyr Pro Gly Asp Ser Asp Thr Ile Tyr Ser
65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Thr Arg Gly Asp Arg Gly Val Asp Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415
Asp Ser Asp Gly Ser Phe Phe Leu Tyr Ser Lys Leu Thr Val Asp Lys
            420                 425                 430
Ser Arg Trp Gln Gln Gly Asn Val Phe Ser Cys Ser Val Met His Glu
        435                 440                 445
Ala Leu His Asn His Tyr Thr Gln Lys Ser Leu Ser Leu Ser Pro Gly
    450                 455                 460
Lys Gly Ser Ser Ser Lys Glu Pro Leu Arg Pro Arg Cys Arg Pro Ile
465                 470                 475                 480
Asn Ala Thr Leu Ala Val Glu Lys Glu Gly Cys Pro Val Cys Ile Thr
                485                 490                 495
Val Asn Thr Thr Ile Cys Ala Gly Tyr Cys Pro Thr Met Thr Arg Val
            500                 505                 510
Leu Gln Gly Val Leu Pro Ala Leu Pro Gln Val Val Cys Asn Tyr Arg
        515                 520                 525
Asp Val Arg Phe Glu Ser Ile Arg Leu Pro Gly Cys Pro Arg Gly Val
    530                 535                 540
Asn Pro Val Val Ser Tyr Ala Val Ala Leu Ser Cys Gln Cys Ala Leu
545                 550                 555                 560
Cys Arg Arg Ser Thr Thr Asp Cys Gly Gly Pro Lys Asp His Pro Leu
                565                 570                 575
Thr Cys Asp Asp Pro Arg Phe Gln Asp Ser Ser Ser Ser Lys Ala Pro
            580                 585                 590
Pro Pro Ser Leu Pro Ser Pro Ser Arg Leu Pro Gly Pro Ser Asp Thr
        595                 600                 605
Pro Ile Leu Pro Gln
    610

<210> SEQ ID NO 11
<211> LENGTH: 1325
<212> TYPE: DNA
<213> ORGANISM: Homo sapiens

<400> SEQUENCE: 11

```
aagcttcacc atgggatgga gctgtatcat cctcttcttg gtggccacag ctaccggtgt    60
ccactccgac atccagatga cccagtctcc atcctcactg tctgcatctg taggagacag   120
agtcaccatc acttgtcggg cgagtcaggg tattagcagg tggttagcct ggtatcagca   180
gaaaccagag aaagccccta agtccctgat ctatgctgca tccagtttgc aaagtggggt   240
cccatcaagg ttcagcggca gtggatctgg gacagatttc actctcacca tcagcggcct   300
gcagcctgaa gattttgcaa cttattactg ccaacagtat aatagttacc ctcggacgtt   360
cggccaaggg accaaggtgg aaatcaaagg agggggcggt tccggaggag cggcagcgg   420
gggaggaggt agcgaggtgc agctggtgca gtctggagca gaggtgaaaa agcccgggga   480
gtctctgagg atctcctgta agggttctgg agacagtttt accacctact ggatcggctg   540
ggtgcgccag atgcccggga aaggcctgga gtggatgggg atcatctatc ctggtgactc   600
tgataccata tacagcccgt ccttccaagg ccaggtcacc atctcagccg acaagtccat   660
cagcaccgcc tacctgcagt ggagcagcct gaaggcctcg gacaccgcca tgtattactg   720
tacgagaggg gaccgggggcg ttgactactg gggccaggga accctggtca ccgtctcctc   780
aggctctacc ggtgggggag gctcgagctc caaggagccg cttcggccac ggtgccgccc   840
catcaatgcc accctggctg tggagaagga gggctgcccc gtgtgcatca ccgtcaacac   900
```

-continued

```
caccatctgt gccggctact gccccaccat gacccgcgtg ctgcaggggg tcctgccggc    960
cctgcctcag gtggtgtgca actaccgcga tgtgcgcttc gagtccatcc ggctccctgg   1020
ctgcccgcgc ggcgtgaacc ccgtggtctc ctacgccgtg gctctcagct gtcaatgtgc   1080
actctgccgc cgcagcacca ctgactgcgg gggtcccaag gaccacccct tgacctgtga   1140
tgacccccgc ttccaggact cctcttcctc aaaggcccct ccccccagcc ttccaagtcc   1200
atcccgactc ccggggccct cggacacccc gatcctccca caataagcgg ccgcagaaca   1260
gaaactcatc tcagaagagg atctgaatgg cgccgcacat caccatcatc accattgatt   1320
ctaga                                                              1325
```

<210> SEQ ID NO 12
<211> LENGTH: 411
<212> TYPE: PRT
<213> ORGANISM: Homo sapiens

<400> SEQUENCE: 12

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Gly Ile
        35                  40                  45

Ser Arg Trp Leu Ala Trp Tyr Gln Gln Lys Pro Glu Lys Ala Pro Lys
    50                  55                  60

Ser Leu Ile Tyr Ala Ala Ser Ser Leu Gln Ser Gly Val Pro Ser Arg
65                  70                  75                  80

Phe Ser Gly Ser Gly Ser Gly Thr Asp Phe Thr Leu Thr Ile Ser Gly
                85                  90                  95

Leu Gln Pro Glu Asp Phe Ala Thr Tyr Tyr Cys Gln Gln Tyr Asn Ser
            100                 105                 110

Tyr Pro Arg Thr Phe Gly Gln Gly Thr Lys Val Glu Ile Lys Gly Gly
        115                 120                 125

Gly Gly Ser Gly Gly Gly Gly Ser Gly Gly Gly Ser Glu Val Gln
    130                 135                 140

Leu Val Gln Ser Gly Ala Glu Val Lys Lys Pro Gly Glu Ser Leu Arg
145                 150                 155                 160

Ile Ser Cys Lys Gly Ser Gly Asp Ser Phe Thr Thr Tyr Trp Ile Gly
                165                 170                 175

Trp Val Arg Gln Met Pro Gly Lys Gly Leu Glu Trp Met Gly Ile Ile
            180                 185                 190

Tyr Pro Gly Asp Ser Asp Thr Ile Tyr Ser Pro Ser Phe Gln Gly Gln
        195                 200                 205

Val Thr Ile Ser Ala Asp Lys Ser Ile Ser Thr Ala Tyr Leu Gln Trp
    210                 215                 220

Ser Ser Leu Lys Ala Ser Asp Thr Ala Met Tyr Tyr Cys Thr Arg Gly
225                 230                 235                 240

Asp Arg Gly Val Asp Tyr Trp Gly Gln Gly Thr Leu Val Thr Val Ser
                245                 250                 255

Ser Gly Ser Thr Gly Gly Gly Ser Ser Ser Lys Glu Pro Leu Arg
            260                 265                 270

Pro Arg Cys Arg Pro Ile Asn Ala Thr Leu Ala Val Glu Lys Glu Gly
        275                 280                 285
```

```
Cys Pro Val Cys Ile Thr Val Asn Thr Thr Ile Cys Ala Gly Tyr Cys
        290                 295                 300

Pro Thr Met Thr Arg Val Leu Gln Gly Val Leu Pro Ala Leu Pro Gln
305                 310                 315                 320

Val Val Cys Asn Tyr Arg Asp Val Arg Phe Glu Ser Ile Arg Leu Pro
                325                 330                 335

Gly Cys Pro Arg Gly Val Asn Pro Val Val Ser Tyr Ala Val Ala Leu
            340                 345                 350

Ser Cys Gln Cys Ala Leu Cys Arg Arg Ser Thr Thr Asp Cys Gly Gly
        355                 360                 365

Pro Lys Asp His Pro Leu Thr Cys Asp Asp Pro Arg Phe Gln Asp Ser
    370                 375                 380

Ser Ser Ser Lys Ala Pro Pro Ser Leu Pro Ser Pro Ser Arg Leu
385                 390                 395                 400

Pro Gly Pro Ser Asp Thr Pro Ile Leu Pro Gln
                405                 410

<210> SEQ ID NO 13
<211> LENGTH: 5
<212> TYPE: PRT
<213> ORGANISM: Homo sapiens

<400> SEQUENCE: 13

Thr Tyr Trp Ile Gly
1               5

<210> SEQ ID NO 14
<211> LENGTH: 17
<212> TYPE: PRT
<213> ORGANISM: Homo sapiens

<400> SEQUENCE: 14

Ile Ile Tyr Pro Gly Asp Ser Asp Thr Ile Tyr Ser Pro Ser Phe Gln
1               5                   10                  15

Gly

<210> SEQ ID NO 15
<211> LENGTH: 7
<212> TYPE: PRT
<213> ORGANISM: Homo sapiens

<400> SEQUENCE: 15

Gly Asp Arg Gly Val Asp Tyr
1               5

<210> SEQ ID NO 16
<211> LENGTH: 11
<212> TYPE: PRT
<213> ORGANISM: Homo sapiens

<400> SEQUENCE: 16

Arg Ala Ser Gln Gly Ile Ser Arg Trp Leu Ala
1               5                   10

<210> SEQ ID NO 17
<211> LENGTH: 7
<212> TYPE: PRT
<213> ORGANISM: Homo sapiens

<400> SEQUENCE: 17

Ala Ala Ser Ser Leu Gln Ser
```

-continued

<210> SEQ ID NO 18
<211> LENGTH: 9
<212> TYPE: PRT
<213> ORGANISM: Homo sapiens

<400> SEQUENCE: 18

Gln Gln Tyr Asn Ser Tyr Pro Arg Thr
1               5

<210> SEQ ID NO 19
<211> LENGTH: 143
<212> TYPE: PRT
<213> ORGANISM: Homo sapiens

<400> SEQUENCE: 19

Ser Lys Glu Pro Leu Arg Pro Arg Cys Arg Pro Ile Asn Ala Thr Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Thr Arg Val Leu Gln Gly Val
        35                  40                  45

Leu Pro Ala Leu Pro Gln Val Val Cys Asn Tyr Arg Asp Val Arg Phe
    50                  55                  60

Glu Ser Ile Arg Leu Pro Gly Cys Pro Arg Gly Val Asn Pro Val Val
65                  70                  75                  80

Ser Tyr Ala Val Ala Leu Ser Cys Gln Cys Ala Leu Cys Arg Arg Ser
                85                  90                  95

Thr Thr Asp Cys Gly Gly Pro Lys Asp His Pro Leu Thr Cys Asp Asp
            100                 105                 110

Pro Arg Phe Gln Asp Ser Ser Ser Lys Ala Pro Pro Pro Ser Leu
        115                 120                 125

Pro Ser Pro Ser Arg Leu Pro Gly Pro Ser Asp Thr Pro Ile Leu
    130                 135                 140

<210> SEQ ID NO 20
<211> LENGTH: 9
<212> TYPE: PRT
<213> ORGANISM: Homo sapiens

<400> SEQUENCE: 20

Asp Val Arg Phe Glu Ser Ile Arg Leu
1               5

<210> SEQ ID NO 21
<211> LENGTH: 9
<212> TYPE: PRT
<213> ORGANISM: Homo sapiens

<400> SEQUENCE: 21

Tyr Arg Asp Val Arg Phe Glu Ser Ile
1               5

<210> SEQ ID NO 22
<211> LENGTH: 9
<212> TYPE: PRT
<213> ORGANISM: Homo sapiens

<400> SEQUENCE: 22

Leu Arg Pro Arg Cys Arg Pro Ile Asn

<210> SEQ ID NO 23
<211> LENGTH: 9
<212> TYPE: PRT
<213> ORGANISM: Homo sapiens

<400> SEQUENCE: 23

Ser Arg Leu Pro Gly Pro Ser Asp Thr
1               5

<210> SEQ ID NO 24
<211> LENGTH: 9
<212> TYPE: PRT
<213> ORGANISM: Homo sapiens

<400> SEQUENCE: 24

Cys Arg Pro Ile Asn Ala Thr Leu Ala
1               5

<210> SEQ ID NO 25
<211> LENGTH: 9
<212> TYPE: PRT
<213> ORGANISM: Homo sapiens

<400> SEQUENCE: 25

Leu Pro Gly Pro Ser Asp Thr Pro Ile
1               5

<210> SEQ ID NO 26
<211> LENGTH: 9
<212> TYPE: PRT
<213> ORGANISM: Homo sapiens

<400> SEQUENCE: 26

Cys Pro Arg Gly Val Asn Pro Val Val
1               5

<210> SEQ ID NO 27
<211> LENGTH: 9
<212> TYPE: PRT
<213> ORGANISM: Homo sapiens

<400> SEQUENCE: 27

Arg Pro Ile Asn Ala Thr Leu Ala Val
1               5

<210> SEQ ID NO 28
<211> LENGTH: 9
<212> TYPE: PRT
<213> ORGANISM: Homo sapiens

<400> SEQUENCE: 28

Val Ala Leu Ser Cys Gln Cys Ala Leu
1               5

<210> SEQ ID NO 29
<211> LENGTH: 294
<212> TYPE: DNA
<213> ORGANISM: Homo sapiens

<400> SEQUENCE: 29
gaggtgcagc tggtgcagtc tggagcagag gtgaaaaagc ccggggagtc tctgaagatc        60
tcctgtaagg gttctggata cagctttacc agctactgga tcggctgggt gcgccagatg       120

```
cccgggaaag gcctggagtg gatggggatc atctatcctg gtgactctga taccagatac      180
agcccgtcct tccaaggcca ggtcaccatc tcagccgaca gtccatcag caccgcctac       240 ctgcagtgga gcagcctgaa ggcctcggac accgccatgt attactgtgc gaga            294
```

<210> SEQ ID NO 30
<211> LENGTH: 98
<212> TYPE: PRT
<213> ORGANISM: Homo sapiens

<400> SEQUENCE: 30

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg
```

<210> SEQ ID NO 31
<211> LENGTH: 285
<212> TYPE: DNA
<213> ORGANISM: Homo sapiens

<400> SEQUENCE: 31

```
gacatccaga tgacccagtc tccatcctca ctgtctgcat ctgtaggaga cagagtcacc      60
atcacttgtc gggcgagtca gggtattagc agctggttag cctggtatca gcagaaacca     120
gagaaagccc ctaagtccct gatctatgct gcatccagtt tgcaaagtgg ggtcccatca     180
aggttcagcg gcagtggatc tgggacagat ttcactctca ccatcagcag cctggagcct     240
gaagattttg caacttatta ctgccaacag tataatagtt accct                      285
```

<210> SEQ ID NO 32
<211> LENGTH: 95
<212> TYPE: PRT
<213> ORGANISM: Homo sapiens

<400> SEQUENCE: 32

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95
```